United States Patent [19]

Greenwood et al.

[11] Patent Number: 5,399,565
[45] Date of Patent: * Mar. 21, 1995

[54] PYRAZOLIDINONE CCK AND GASTRIN ANTAGONISTS AND PHARMACEUTICAL FORMULATIONS THEROF

[75] Inventors: Beverley Greenwood, Fishers; David R. Helton, Greenfield, both of Ind.; J. Jeffry Howbert, Bellevue, Wash.; Steven J. Mitan; Kurt Rasmussen, both of Indianapolis, Ind.

[73] Assignee: Eli Lilly and Company, Indianapolis, Ind.

[*] Notice: The portion of the term of this patent subsequent to Apr. 5, 2011 has been disclaimed.

[21] Appl. No.: 151,608

[22] Filed: Nov. 12, 1993

Related U.S. Application Data

[63] Continuation-in-part of Ser. No. 33,737, Mar. 18, 1993, Pat. No. 5,300,519, which is a continuation of Ser. No. 982,257, Nov. 25, 1992, abandoned, which is a continuation of Ser. No. 737,624, Jul. 30, 1991, abandoned, which is a continuation-in-part of Ser. No. 553,489, Jul. 17, 1990, abandoned.

[51] Int. Cl.$^6$ ............................................. A61K 31/415
[52] U.S. Cl. ..................................... 514/314; 514/338; 514/341; 514/407; 546/146; 546/147; 546/174; 546/175; 548/364.4; 548/364.7; 548/369.4; 548/369.7; 548/370.4; 548/366.1
[58] Field of Search ............... 514/314, 338, 341, 407; 546/146, 147, 174, 175; 548/364, 367, 374

[56] References Cited

U.S. PATENT DOCUMENTS

| | | | |
|---|---|---|---|
| 3,312,550 | 4/1967 | Stewart et al. | |
| 3,957,814 | 5/1976 | Moller et al. | 424/273 |
| 4,081,596 | 3/1978 | Moller et al. | 548/367 |
| 4,902,708 | 2/1990 | Kim | 514/419 |
| 5,153,191 | 10/1992 | Woodruff | 514/221 |
| 5,300,514 | 4/1994 | Brown et al. | 514/314 |

FOREIGN PATENT DOCUMENTS

| | | |
|---|---|---|
| 0155523 | 9/1985 | European Pat. Off. . |
| 0166355 | 1/1986 | European Pat. Off. . |
| 0373512 | 6/1990 | European Pat. Off. . |
| 0411668 | 2/1991 | European Pat. Off. . |
| 2529786 | 1/1984 | France . |
| 767705 | 2/1957 | United Kingdom . |
| 1260939 | 1/1972 | United Kingdom . |

OTHER PUBLICATIONS

Neitzel et al., *Liebigs Ann. Chem.*, 1907–1912 (1980).
Howbert et al., Multiple Cholecystokinin Receptors—Progress Toward CNS Therapeutic Targets Abstract, Harlow, England, Sep. 20–22, 1990.
Hodgkiss, et al. Multiple Cholecystokinin Receptors—Progress Toward CNS Therapeutic Targets Abstract, Harlow, England, Sep. 20–22, 1990.
Lucaites et al., Soc. Neurosci. Abstr. 16:82, 1990.
Howbert et al., Soc. Neurosci. Abstr. 16:82, 1990.
Howbert, Joint Great Lakes–Central Regional Meeting of American Chemical Society, Indianapolis, Ind., May 29–31, 1991.
Howbert, Invited Lectures, McGill University (Nov. 28, 1990), Univ. Sherbrook (Nov. 29, 1990), Indiana Univ. School of Med. (Dec. 4, 1990; Dec. 6, 1990), Johns Hopkins Univ. (Jan. 29, 1991) Howbert, Society for Drug Research, London, England, Mar. 21, 1991.
Rasmussen, Methods of Evaluation for Psychopharmacology, Butler Universty, Indianapols, Ind., Apr. 23, 1993.

(List continued on next page.)

*Primary Examiner*—C. Warren Ivy
*Assistant Examiner*—Raymond Covington
*Attorney, Agent, or Firm*—MaCharri R. Vorndran-Jones

[57] ABSTRACT

Novel substituted pyrazolidinones have been found to exhibit significant binding to cholecystokinin (CCK) receptors and gastrin receptors in the brain and/or peripheral sites such as the pancreas, stomach, and ileum. The pyrazolidinones are CCK and gastrin receptor antagonists and find therapeutic application in the treatment of gastrointestinal disorders, central nervous system disorders and for appetite regulation in warm-blood vertebrates. Pharmaceutical formulations for such indications are described.

19 Claims, No Drawings

OTHER PUBLICATIONS

Howbert et al., LY288513, an Antagonist of Brain Cholecystokinin Receptors, American College of Neurospychopharmacology, San Juan, Puerto Rico, Dec. 14–18, 1992.

Palmour et al., Anxiogenic Effects of CCK Agonists in a Non–human Primate Model: Central or Peripheral?, International Symposium, Chatham, Mass., May 19–22, 1993.

Howbert et al., Differential Ability of a Pyrazolidinone Type A CCK Receptor Antagonist to Block the Gastric Inhibitory and Pyloric Contractile Actions of CCK, International Symposium, Chatham, Mass., May 19–22, 1993.

Howbert et al., $CCK_B$ Receptors Tonically Modulate a 10 Dopaminergic Neurons: Neurochemical Evaluation of LY288513, Annual Society for Neuroscience Meeting, Washington, D.C., Nov. 7–12, 1993.

Tollefson, CCK Antagonist and Other Related Neuropeptides as Anxiolytics, First International Congress on Hormones, Brain and Neuropsychopharmacology, Sep. 1993.

Schmidt et al., Behavioral and Electrophysiological Characterization of the New Cholecystokinin (CCK)-B Antagonist LY288513, Society for Neuroscience Meeting, Washington, D.C., Nov. 1993.

Hughes et al., Development of a Class of Selective Cholecystokinin Type B Receptor Antagonists having Potent Anxiolytic Activity, Proc. Natl., Acad. Sci. USA, 87:6728–6732, 1990.

Bock, Development of Non-Peptide Cholecystokinin Type B Receptor Antagonists, Drugs of the Future, 16(7):631–640, 1991.

Staley et al., CCK Antagonists Interact with CCK-B Receptors on Human Small Cell Lung Cancer Cells, Peptides, 11(5):1033–6, Sep.–Oct., 1990.

Greenwood et al., Mechanisms by Which CCK-8 Stimulates Gallbladder and Colonic Motility in the Ferret, American Gastroenterological Association/American Association for the Study of Liver Diseases, Abstr., Boston, Mass., May 16–19, 1993.

Greenwood et al., CCK-8 Contracts the Gallbladder and Colon Through Different Mechanisms in the Ferret, New York Academy of Sciences, Jul. 15, 1993.

Singh et al., The Antagonism of Benzodiazepine Withdrawal Effects by the Selective Cholecystokinin $_B$ B Receptor Antagonist CI-988, Br. J. Pharmacol., 105, 8–100, 1992.

Rasmussen et al., The CCK-B Antagonist LY288513 Blocks Diazepam-Withdrawal-Induced Increases in Auditory Startle Response, Abstr., New York Academy of Sciences, Jul. 15, 1993.

Rasmussen, CCK, Schizophrenia, and Anxiety: CCK-B Antagonists Inhibit the Activity of Brain Dopamine Neurons, New York Academy of Sciences Jul. 15, 1993.

Rasmussen et al., Electrophysiological Effects of Diphenylpyrazolidinone CCK-B and CCK-A Antagonists on Midbrain Dopamine Neurons, The Journal of Pharmacology and Experimental Therapeutics, (accepted Sep. 1992).

Iyengar, $CCK_B$ Receptors Tonically Modulate A10 Dopaminergic Neurons: Neurochemical Evaluation of LY288513, International Symposium, Cape Cod, May 19–22, 1993.

Boyce et al., Modulatory Role for CCK-B Antagonists in Parkinson's Disease, Clinical Neuropharmacology, 13:339–347, 1990.

Rasmussen, Quinazolinone CCK-B Antagonists Decrease the Number of Spontaneously Active Dopamine Neurons, Society for Neuroscience Convention, Anaheim, Calif., Oct. 26, 1992.

Rasmussen et al., Cholecystokinin (CCK) and Schizophrenia: The Selective $CCK_B$ Antagonist LY262691 Decreases Midbrain Dopamine Unit Activity, European Journal of Pharmacology, 209:135–138, 1991.

Palmour et al., Anxiogenic and Cardiovascular Effects of CCK-4 in Monkeys are Blocked by the CCK-B Antagonist LY262691, Society for Neuroscience Meeting, 1991 Annual Meeting, New Orleans, La., Aug. 1991.

Howbert et al., A Novel Series of Non-Peptide CCK and Gastrin Antagonists: Medicinal Chemistry and Electrophysiological Demonstration of Antagonism, CCK symposium, Harlow, England, Oxford University Press 29–37, 1992.

(List continued on next page.)

OTHER PUBLICATIONS

Totterdell et al., Cholecystokinin–Immunoreactive Boutons in Synaptic Contact with Hippocampal Pyramidal Neurons that Project to the Nucleus Accumbens, Neuroscience, 19:181–192, 1986.

Rasmussen et al., Electrophysiological Effects of Diphenylpyrazolidinone Cholecystokinin-B and Cholecystokinin-A Antagonists on Midbrain Dopamine Neurons, Journal of Pharmacology and Experimental Therapeutics, 264:480–488, 1993 (Accepted Sep. 8, 1992).

Rasmussen et al., Inihbition of A9 and A10 Dopamine Cells by the Cholecystokinin-B Antagonist LY262691: Mediation Through Feedback Pathways From Forebrain Sites, Synapse, 15:95–103, 1993.

Rasmussen et al., The CCK-B Antagonist LY288513 Blocks Effects of Diazepam Withdrawal on Auditory Startle, NeuroReport, 5:154–156, 1993.

Yu, et al., Quinazolinone CCK-B antagonists decrease the number of spontaneously active dopamine neurons, Soc. for Neurosc. Abstr. (1992)278.

PYRAZOLIDINONE CCK AND GASTRIN ANTAGONISTS AND PHARMACEUTICAL FORMULATIONS THEROF

CROSS REFERENCE

This application is a continuation-in-part of Ser. No. 08/033,737, filed Mar. 18, 1993, now U.S. Pat. No. 5,300,519, which is a continuation of application Ser. No. 07/982,257, (now abandoned), filed Nov. 25, 1992, which is a continuation of Ser. No. 07/737,624, filed Jul. 30, 1991, (now abandoned), which is a continuation-in-part of Ser. No. 07/553,489, filed Jul. 17, 1990, (now abandoned).

BACKGROUND AND SUMMARY OF THE INVENTION

This invention relates to biologically active pyrazolidinones. More particularly, this invention is directed to methods for using certain substituted pyrazolidinones which bind to receptors for cholecystokinin (CCK), e.g., those of the brain and pancreas, and to receptors for gastrin, e.g., those of the stomach. The compounds are CCK and gastrin antagonists which are useful in the treatment and prevention of CCK and gastrin-related disorders of the gastrointestinal, central nervous and appetite regulatory systems of warm-blooded vertebrates, especially humans. Examples of such disorders which may be treated using the compounds of this invention include psychosis, anxiety disorders, benzodiazepine cessation and withdrawal, nicotine cessation and withdrawal, smoking cessation, neuroleptic related extrapyramidal motor syndromes, gastrointestinal neoplasms, irritable bowel syndrome and other gastrointestinal motility disorders.

BACKGROUND OF THE INVENTION

Cholecystokinin (CCK) is a neuropeptide found in both gastrointestinal tissue and the tissues of the central nervous system. CCK is believed to play an important role in appetite regulation. Among the effects of CCK are inhibition of gastric emptying, stimulation of gall bladder contraction, stimulation of pancreatic enzyme secretion, and stimulation of colonic motility. Gastrin is a neuropeptide found particularly in the gastrointestinal tract. It is one of the primary natural stimulators of gastric acid secretion. It also has growth stimulatory effects on a variety of gastrointestinal tissues. CCK and gastrin antagonists are useful in the treatment and prevention of CCK and gastrin-related disorders of the gastrointestinal and central nervous systems, as well as modulation of the appetite regulatory systems of warm-blooded vertebrates.

In man and animals administration of CCK stimulates colonic motility in a manner that is similar to the pattern of colonic motility seen after eating. Harvey et al., Lancet 1:1–3 (1973). Compounds which inhibit CCK-induced colonic motility and do not significantly inhibit gall bladder contraction are particularly preferred for use in treating or preventing irritable bowel syndrome, non-ulcer dyspepsia, and idiopathic constipation.

CCK reportedly coexists with dopamine in certain mid-brain neurons and thus may also play a role in the functioning of dopaminergic systems in the brain. The CCK/gastrin receptor family is thought to contain three receptor subtypes, for which the location of the prototype receptor is given in parentheses: CCK-A (pancreas), CCK-B (brain), and gastrin (stomach fundus).

Several classes of CCK receptor antagonists have been reported in the literature. One class comprises derivatives of cyclic nucleotides, for example, dibutyryl cyclic GMP. Another art recognized class of CCK antagonists comprise the C-terminal fragments and analogs of CCK. Another class of CCK receptor antagonists are amino acid derivatives including proglumide, a derivative of glutaramic acid, and the N-acyltryptophanes such as p-chlorobenzoyl-L-tryptophan. More recently certain substituted amino phenyl compounds were described as CCK antagonists in published European Patent Application 0166355. Because of the wide range of potential clinical applications of CCK binding compounds, intensive research have been ongoing to define other compounds exhibiting CCK receptor binding properties.

SUMMARY OF THE INVENTION

This invention is directed to novel pyrazolidinone compounds of Formula I or II below which have been found to exhibit CCK activity and methods for using said compounds. These compounds are useful in the treatment and prevention of CCK-related disorders of the gastrointestinal and central nervous systems, as well as in modulating the appetite regulatory systems of warm-blooded vertebrates, especially humans. As CCK antagonists, they may be particularly useful in the treatment and prevention of gastrointestinal ulcers, and of neoplasms of gastrointestinal origin. Further, the compounds are indicated for use in the treatment of gastrointestinal motility disorders.

The compounds of Formula I or II are useful for the treatment or prevention of neuroleptic related disorders including dystonia, dyskinesia, akathisia, and Parkinsonism. Additionally, these compounds are particularly useful for CCK-related conditions such as psychosis, anxiety and anxiety related disorders, benzodiazepine cessation and withdrawal, nicotine cessation and withdrawal, and cessation of smoking.

DETAILED DESCRIPTION OF THE INVENTION

This invention is directed to compounds of the formula

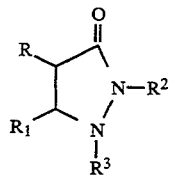

I or

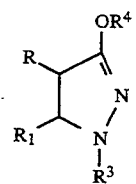

II wherein

R and $R^1$ are independently hydrogen, $C_1$-$C_6$ alkyl, phenyl, benzyl, naphthyl, pyridyl or substituted phenyl having 1, 2, or 3 substituents selected from the group consisting of $C_1$-$C_6$ alkyl, $C_1$-$C_6$ alkoxy, $C_1$-$C_6$ alkylthio, halo, trifluoromethyl, phenyl, phenoxy, phenyl($C_1$-$C_4$ alkyl), phenyl($C_1$-$C_4$ alkoxy), phenylacetyl, $C_1$-$C_6$ alkanoyl, cyano, carbamyl, nitro, $C_1$-$C_6$ alkoxycarbonyl, methylenedioxy, $C_{3-6}$ alkylene, amino, —NH($C_1$-$C_4$ alkyl or benzyl), and N($C_1$-$C_4$ alkyl)$_2$;

$R^2$ is hydrogen, $C_1$-$C_6$ alkyl, carboxymethyl, $C_1$-$C_4$ alkoxycarbonylmethyl or a group of the formula

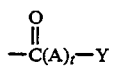

wherein
t is 1 or 0;
A is —CH$_2$—, —O—, —NH— or —N($C_1$-$C_6$ alkyl)—; and
Y is phenyl or substituted phenyl as defined above;
$R_4$ is $C_1$-$C_6$ alkyl, carboxymethyl, or $C_1$-$C_4$ alkoxycarbonylmethyl;
$R^3$ is hydrogen or a group of the formula

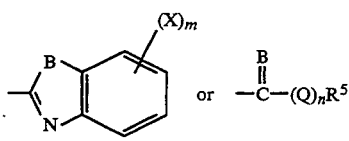

wherein
B is O or S;
X is selected from the phenyl substituents defined above;
m is 0, 1 or 2;
n is 0 or 1;
Q is —NH—, —N($C_1$-$C_6$ alkyl)—, —S—, or —O—; and
$R^5$ is a group of the formula —[CH($R^6$)]$_q$—(CH$_2$)$_r$—$R^7$
wherein
$R^6$ is hydrogen or $C_1$-$C_6$ alkyl;
q is 0 or 1;
r is 0, 1 or and $R^7$ is hydrogen, $C_1$-$C_8$ alkyl, $C_{3-8}$ cycloalkyl, pentafluorophenyl, pyridyl, tetrahydro-naphthyl, indolyl, quinolinyl, phenyl, naphthyl, or phenyl or naphthyl substituted with 1, 2, or 3 substituents as defined above for phenyl; or
the group —(Q)$_n$$R^5$ is 2-tetrahydroisoquinolinyl; and
the pharmaceutically acceptable salts thereof;
provided that at least one of the groups R or $R^1$ is other than hydrogen or $C_1$-$C_6$ alkyl, and R or $R^1$ is hydrogen only when the other of R and $R^1$ is substituted phenyl in which the substituent is phenyl; and provided further that at least one of the groups $R^2$ and $R^3$ is other than hydrogen, and when $R^3$ is a group of the formula

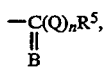

$R^2$ is other than a group of the formula

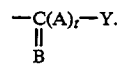

In the compounds of Formula I or II, the groups R and $R^1$ can be in either the cis or trans configuration relative to the plane of the pyrazolidinone ring. The trans configuration, preferred in accordance with the present invention, is indicated to be the thermodynamically favored form.

As used herein "halo" refers to fluoro, chloro, or bromo. The term "$C_1$-$C_6$ alkyl" includes both straight and branched chain alkyl and cycloalkyl and includes methyl, ethyl, propyl, cyclopropyl, isopropyl, butyl, methylcyclopropyl, cyclobutyl, isobutyl, t-butyl, pentyl, cyclopentyl, neopentyl, hexyl, cyclohexyl, 2-methylpentyl and the like. In the "$C_1$-$C_6$ alkoxy" and "$C_1$-$C_6$ alkylthio" substituents, the alkyl portion is $C_1$-$C_6$ alkyl as defined above. The term "$C_1$-$C_6$ alkanoyl" includes formyl, acetyl, propionyl, butyryl, pentanoyl, hexanoyl, and the like.

The term "pharmaceutically acceptable salts" encompasses those salts that form by standard acid-base reactions with basic groups (such as amino groups) and acidic groups, particularly carboxylic acid groups, on the compounds of Formula I or II. Thus, the pharmaceutically acceptable salts of the present invention can be prepared by conventional chemical methods from the compounds of Formula I or II which contain a basic or acidic moiety. The artisan will recognize that the compound nucleus of Formula I or II may be intrinsically acidic. Thus, the pyrazolidinone nucleus can be the acidic moiety which forms salts. Generally, the salts are prepared by reacting the free base or acid with a stoichiometric amount or with an excess of the desired salt-forming acid or base in a suitable solvent or combination of solvents. Suitable salt-forming acids include inorganic acids such as hydrochloric, hydrobromic, sulfuric, sulfamic, phosphoric, t0 nitric, and the like; organic acids such as acetic, propionic, succinic, glycolic, stearic, lactic, citric, malic, tartaric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethanedisulfonic, oxalic, benzenesulfonic, picric, cinnamic, and like acids. Bases which find use for preparation of salts of compounds of Formula I or II having an acidic moiety include alkali or alkaline earth metal hydroxides such as sodium, potassium, lithium, calcium, or magnesium hydroxides, ammonia, or organic bases such as benzylamine, dibenzylamine, dibenzylethylenediamine, triethylamine, trimethylamine, piperidine, pyrrolidine, 2-hydroxyethylamine, bis(2-hydroxyethyl)amine, phenylethylbenzylamine, and like organic amines.

The artisan will recognize that the term "gastrointestinal" refers to the stomach, pancreas, intestines, and colon. See, Devlin, *Textbook of Biochemistry with Clinical Correlations,* 1134–1135 (John Wiley & Sons, New York; 1982). Thus, the phrase "neoplasms of gastrointestinal origin" refers to neoplasms originating from the stomach, pancreas, intestines, and colon. The artisan will recognize that the phrase "neoplasm" includes both malignant and benign tissue growth.

The term "gastrointestinal motility disorders" and "functional bowel disorder associated with motility disorders" refer to conditions characterized by abnormal bowel function without detectable structural abnormalities. Abnormal bowel function includes diarrhea, constipation, mucorrhea, and pain or discomfort over the course of the sigmoid colon. The terms include, but are not limited to, irritable bowel syndrome, non-ulcer dyspepsia, idiopathic constipation, gastric hypermotility, and colonic hypermotility.

The compounds of this invention bind to CCK and gastrin receptors in the brain and/or peripheral sites such as the pancreas, gall bladder, stomach, ileum and colon. Their ability to antagonize CCK and gastrin makes these compounds useful as pharmaceutical agents for the treatment and prevention of disease states wherein CCK or gastrin may be involved. Examples of said disease states include gastrointestinal disorders such as irritable bowel syndrome, ulcers, excess pancreatic or gastric secretion, acute pancreatitis, motility disorders, gastric hypermotility, colonic hypermotility, and neoplasms of gastrointestinal origin. Additional examples include central nervous system disorders involving CCK's interaction with dopamine, such as neuroleptic-related extrapyramidal motor syndromes (including tardive dyskinesia, dystonia, acute dystonia, akathisia, and Parkinsonism), Parkinson's disease, psychosis, and Gilles de la Tourette Syndrome.

These compounds are useful for other CNS disorders where CCK is believed to be a causative factor, such as panic attacks and other forms of anxiety, and in modulating appetite regulatory systems. The term "modulation of appetite regulatory systems" includes but is not limited to regulation of the undesired urge to consume food, nicotine, and/or benzodiazepines.

The skilled artisan will recognize that psychotic conditions are characterized by hallucinations, delusions, or grossly disorganized behavior which indicate that the patient suffers from gross impairment in the patients' conception of reality. One common psychotic condition is schizophrenia. Drugs having antipsychotic activity can be useful for treating a variety of important psychotic disorders.

Pathological psychological conditions which are psychoses, or may be associated with psychotic features include, but are not limited to the following disorders which have been characterized in the DSM-III-R. *Diagnostic and Statistical Manual of Mental Disorders*, Revised, 3rd Ed. (1980). The DSM-III-R was prepared by the Task Force on Nomenclature and Statistics of the American Psychiatric Association, and provides clear descriptions of diagnostic categories. The skilled artisan will recognize that there are alternative nomenclatures, nosologies, and classification systems for pathologic psychological conditions and that these systems evolve with medical scientific progress.

Examples of pathologic psychologic conditions which may be treated using the compounds of this invention include, but are not limited to, Moderate Mental Retardation (318.00), Severe Mental Retardation (318.10), Profound Mental Retardation (318.20), Unspecified Mental Retardation (319.00), Autistic Disorder (299.00), Pervasive Development Disorder NOS (299.80), Attention-Deficit Hyperactivity Disorder (314.01), Conduct Disorder, Group Type (312.20), Conduct Disorder, Solitary Agressive Type (312.00), Conduct Disorder, Undifferentiated Type (312.90), Tourette's Disorder (307.23), Chronic Motor or Vocal Tic Disorder (307.22), Transient Tic Disorder (307.21), Tic Disorder NOS (307.20), Primary Degenerative Dementia of the Alzheimer Type, Senile Onset, Uncomplicated (290.00), Primary Degenerative Dementia of The Alzheimer Type, Senile Onset, with Delirium (290.30), Primary Degenerative Dementia of the Alzheimer Type, Senile Onset, with Delusions (390.20), Primary Degenerative Dementia of the Alzheimer Type, Senile Onset, with Depression (290.21), Primary Degenerative Dementia of the Alzheimer Type, Presenile Onset, Uncomplicated (290.10), Primary Degenerative Dementia of the Alzheimer Type, Presenile Onset, with Delirium (290.11), Primary Degenerative Dementia of the Alzheimer Type, Presenile Onset, with Delusions (290.12), Primary Degenerative Dementia of the Alzheimer Type, Presenile Onset, with Depression (290.13), Multi-infarct dementia, Uncomplicated (290.40), Multi-infarct dementia, with Delirium (290.41), Multi-infarct Dementia, with Delusions (290.42), Multi-infarct Dementia, with Depression (290.4 3), Senile Dementia NOS (290.10), Presenile Dementia NOS (290.10), Alcohol Withdrawal Delirium (291.00 ), Alcohol Hallucinosis (291.30), Alcohol Dementia Associated with Alcoholism (291.20), Amphetamine or Similarly Acting Sympathomimetic Intoxication (305.70), Amphetamine or Similarly Acting Sympathomimetic Delusional Disorder (292.11), Cannabis Delusional Disorder (292.11), Cocaine Intoxication (305.60), Cocaine Delirium (292.81), Cocaine Delusional Disorder (292.11), Hallucinogen Hallucinosis (305.30), Hallucinogen Delusional Disorder (292.11), Hallucinogen Mood Disorder (292.84), Hallucinogen Posthallucinogen Perception Disorder (292.89), Phencyclidine (PCP or Similarly Acting Arylcyclohexylamine Intoxication (305.90), Phencyclidine (PCP) or Similarly Acting Arylcyclohexylamine Delirium (292.81), Phencyclidine (PCP) or Similarly Acting Arylcyclohexylamine Delusional Disorder (292.11), Phencyclidine (PCP) or Similarly Acting Arylcyclohexylamine Hood Disorder (292.84), Phencyclidine (PCP) or Similarly Acting Arylcyclohexylamine Organic Mental Disorder NOS (292.90), Other or unspecified Psychoactive Substance Intoxication (305.90), Other or Unspecified Psychoactive Substance Delirium (292.81), Other or Unspecified Psychoactive Substance Dementia (292.82), Other or Unspecified Psychoactive Substance Delusional Disorder (292.11), Other or Unspecified Psychoactive Substance Hallucinosis (292.12), Other or Unspecified Psychoactive Substance Mood Disorder (292.84), Other or Unspecified Psychoactive Substance Anxiety Disorder (292.89), Other or Unspecified Psychoactive Substance Personality Disorder (292.89), Other or Unspecified Psychoactive Substance Organic Mental Disorder NOS (292.90), Delirium (293.00), Dementia (294.10), Organic Delusional Disorder (293.81), Organic Hallucinosis (293.81), Organic Mood Disorder (293.83), Organic Anxiety Disorder (294.80), Organic Personality Disorder (310.10), Organic Mental Disorder (29.80), Obsessive Compulsive Disorder (300.30), Post-traumatic Stress Disorder (309.89), Generalized Anxiety Disorder (300.02), Anxiety Disorder NOS (300.00), Body Dysmorphic Disorder (300.70), Hypochondriasis (or Hypochondriacal Neurosis) (300.70), Somatization Disorder (300.81), Undifferentiated Somatoform Disorder (300.70), Somatoform Disorder NOS (300.70), Intermittent Explosive Disorder (312.34), Kleptomania (312.32), Pathological Gambling (312.31), Pyromania (312.33), Trichotillomania (312.39), and Impulse Control Disorder NOS (312.39).

Additional examples of pathologic psychological conditions which may be treated using the compounds of this invention include Schizophrenia, Catatonic, Subchronic, (295.21), Schizophrenia, Catatonic, Chronic (295.22), Schizophrenia, Catatonic, Subchronic with Acute Exacerbation (295.23), Schizophrenia, Catatonic, Chronic with Acute Exacerbation (295.24), Schizophrenia, Catatonic, in Remission (295.55), Schizophrenia, Catatonic, Unspecified (295.20), Schizophrenia, Disorganized, Chronic (295.12), Schizophrenia, Disorganized, Subchronic with Acute Exacerbation (29 5.13), Schizophrenia, Disorganized, Chronic with Actue Exacerbation (295.14), Schizophrenia, Disorganized, in Remission (295.15), Schizophrenia, Disorganized, Unspecified (295.10), Schizophrenia, Paranoid, Subchronic 295.31), Schizophrenia, Paranoid, Chronic (295.32), Schizophrenia, Paranoid, Subchronic with Acute Exacerbation (295.33), Schizophrenia, Paranoid, Chronic with Actue Exacerbation (295.34), Schizophrenia, Paranoid, in Remission (295.35), Schizophrenia, Paranoid, Unspecified (295.30), Schizophrenia, Undifferentiated, Subchronic (295.91), Schizophrenia, Undifferentiated, Chronic (295.92), Schizophrenia, Undifferentiated, Subchronic with Acute Exacerbation (295.93), Schizophrenia, Undifferentiated, Chronic with Acute Exacerbation (295.94), Schizophrenia, Undifferentiated, in Remission (295.95), Schizophrenia, Undifferentiated, Unspecified (295.90), Schizophrenia, Residual, Subchronic (295.61), Schizophrenia, Residual, Chronic (295.62), Schizophrenia, Residual, Subchronic with Acute Exacerbation (295.63), Schizophrenia, Residual, Chronic with Acute Exacerbation (295.94), Schizophrenia, Residual, in Remission (295.65), Schizophrenia, Residual, unspecified (295.60), Delusional (Paranoid) Disorder (297.10), Brief Reactive Psychosis (298.80), Schizophreniform Disorder (295.40), Schizoaffective Disorder (295.70), induced Psychotic Disorder (297.30), Psychotic Disorder NOS (Atypical Psychosis) (298.90), Bipolar Disorder, Mixed, Severe, without Psychotic Features (296.63), Bipolar Disorder, Manic, Severe, without Psychotic Features (296.43), Bipolar Disorder, Depressed, Severe, without Psychotic Features (296.53), Bipolar Disorder, Mixed, with Psychotic Features (296.64),Bipolar Disorder, Manic, with Psychotic Features (296.44), Bipolar Disorder, Depressed, with Psychotic Features (296.54), Bipolar Disorder NOS (296.70), Major Depression, Single Episode, with Psychotic Features (296.24), Major Depression, Recurrent with Psychotic Features (296.34) Personality Disorders, Paranoid (301.00), Personality Disorders, Schizoid (301.20), Personality Disorders, Schizotypal (301.22), Personality Disorders, Antisocial (301.70), Personality Disorders, Borderline (301.83).

Anxiety disorders which may be treated using the compounds of this invention include, but are not limited to, Anxiety Disorders (235), Panic Disorder (235), Panic Disorder with Agoraphobia (300.21), Panic Disorder without Agoraphobia (300.01), Agoraphobia without History of Panic Disorders (300.22), Social Phobia (300.23), Simple Phobia (300.29), Organic Anxiety Disorder (294.80), Psychoactive Substance Anxiety Disorder (292.89), Separation Anxiety Disorder (309.21), Avoidant Disorder of Childhood or Adolescence (313.21), and Overanxious Disorder (313.00).

Preferably, an effective amount of one or more compounds of this invention or a pharmaceutically acceptable salt thereof, is used for the treatment of the following pathologic psychological conditions: Moderate Mental Retardation; Severe Mental Retardation; Profound Mental Retardation; Autistic Disorder; Attention-Deficit Hyperactivity Disorder; Pervasive Development Disorder NOS; Conduct Disorder, Group Type; Conduct Disorder, Solitary Agressive Type; Tourette's Disorder; Primary Degenerative Dementia of the Alzheimer Type, Senile Onset, with Delirium; Primary Degenerative Dementia of the Alzheimer Type, Senile Onset, with Delusions; Primary Degenerative Dementia of the Alzheimer Type, Presenile Onset; Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis); Bipolar Disorder, Mixed, with Psychotic Features; Bipolar Disorder, Manic, with Psychotic Features; Bipolar Disorder, Depressed, with Psychotic Features; Bipolar Disorder NOS; Major Depression, Single Episode, or Recurrent with Psychotic Features; Personality Disorders, Paranoid; Personality Disorders, Schizoid; Personality Disorders, Schizotypal; Personality Disorders, Antisocial; Personality Disorders, Borderline, Anxiety Disorders, Panic Disorder, Panic Disorder with Agoraphobia, Panic Disorder without Agoraphobia, Agoraphobia without History of Panic Disorders, Social Phobia, Simple Phobia, Obsessive Compulsive Disorder , Post-Traumatic Stress Disorder, Generalized Anxiety Disorder, Anxiety Disorder NOS, Organic Anxiety Disorder , Psychoactive Substance Anxiety Disorder, Separation Anxiety Disorder, Avoidant Disorder of Childhood or Adolescence, and Overanxious Disorder.

More preferredly, one or more compounds of this invention are used to treat the following psychotic conditions: Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified;

Schizophrenia, Paranoid, Subchronic; Schizophrenia, Paranoid, Chronic; Schizophrenia, Paranoid, Subchronic with Actue Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis); Bipolar Disorder, Mixed, with Psychotic Features; Bipolar Disorder, Manic, with Psychotic Features; Bipolar Disorder, Depressed, with Psychotic Features; Bipolar Disorder NOS; Personality Disorders, Paranoid; Personality Disorders, Schizoid; Personality Disorders, Schizotypal; Personality Disorders, Antisocial; Personality Disorders, Borderline.

Examples of psychotic conditions which are most preferredly treated using the compounds of this invention include Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchornic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Personality Disorders, Schizoid; and Personality Disorders, Schizotypal.

Examples of anxiety disorders which are preferredly treated using an effective amount of the compounds of this invention, or a pharmaceutically acceptable salt thereof, include Anxiety Disorders, Panic Disorder, Panic Disorder with Agoraphobia, Panic Disorder without Agoraphobia, Agoraphobia without History of Panic Disorders, Social Phobia, Simple Phobia, Obsessive Compulsive Disorder, Post-Traumatic Stress Disorder, Generalized Anxiety Disorder, Anxiety Disorder NOS, Organic Anxiety Disorder, Psychoactive Substance Anxiety Disorder, Separation Anxiety Disorder, Avoidant Disorder of Childhood or Adolescence, and Overanxious Disorder.

Examples of the anxiety disorders which are most preferredly treated using the compounds of this invention include Panic Disorder; Social Phobia; Simple Phobia; Organic Anxiety Disorder; Obsessive Compulsive Disorder; Post-traumatic Stress Disorder; Generalized Anxiety Disorder; and Anxiety Disorder NOS.

Preferred CCK and gastrin receptor binding compounds of this invention are the pyrazolidinones of Formula I, particularly those wherein R and $R^1$ are in the trans configuration relative to the plane of the pyrazolidinone ring. Preferably, R and $R^1$ are phenyl or substituted phenyl. A preferred group of compounds of Formula I are those wherein $R^2$ is hydrogen and $R^3$ is a group of the formula

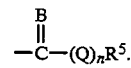

One series of such preferred compounds of this invention are those wherein B is sulfur, n is 1, Q is —NH—, and $R^5$ is phenyl or substituted phenyl.

Another preferred group of compounds exhibiting a consistent pattern of significant binding to CCK and gastrin receptors are those compounds of Formula I wherein $R^2$ is hydrogen and $R^3$ is a moiety defined by the group —CONH—[CH($R^6$)]$_q$—(CH$_2$)$_r$—$R^7$. Especially preferred of those compounds are those wherein q and r are 0 and $R^7$ is phenyl, substituted phenyl, 2-naphthyl or 3-quinolinyl and R and $R^1$ are phenyl, naphthyl, or substituted phenyl in the trans configuration relative to the plane of the pyrazolidinone ring. When $R^7$ is substituted phenyl, preferred substituents are halo, more particularly, chloro, bromo or iodo; trifluoromethyl; $C_1$–$C_4$ alkyl; $C_3$–$C_4$ alkylene; benzyloxy; and methylthio.

The compounds of this invention are readily prepared from the corresponding compounds of the formula

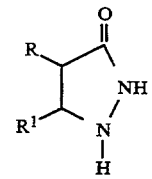

III

The intermediate 3-pyrazolidinones are readily prepared by reacting hydrazine with the corresponding α,β-unsaturated esters of the formula $R^1$—H=C(-R)—COOR' wherein R and $R^1$ are as defined above and R' is an ester forming group, typically $C_1$–$C_6$ alkyl. The present compounds are prepared generally by acylating or alkylating the 3-pyrazolidinones of Formula III under neutral or basic conditions with acylating or alkylating agents selected to give the targeted compound of this invention.

The intermediate 3-pyrazolidinones can be enantioselectively prepared by reacting hydrazine with a compound of the formula

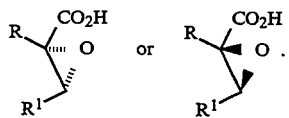

Most preferably, the hydrazine reaction may be run using an aqueous solvent. Other hydrazine-compatible solvents such as ethanol may be used. The product of the hydrazine reaction is reacted with di-tert-butyldicarbonate and dimethylaminopyridine (DMAP) to form a compound of the formula

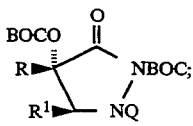

wherein BOC refers to butyloxycarbonyl and Q is hydrogen or butyloxycarbonyl.

The product of the BOC reaction is subject to hydrogenolysis. Most preferably, the hydrogenolysis reaction is effected using dissolving metal reduction or palladium catalyzed hydrogenolysis in the presence of an amine.

More preferredly, the product of the hydrazine reaction is contacted with t-butoxydicarbonate anhydride, DMAP, and a solvent such as acetonitrile, tetrahydrofuran, methylene chloride, or ethyl acetate before subjecting the intermediate pyrazolidinone to palladium catalyzed hydrogenolysis in the presence of a tertiary amine. The product of the hydrogenolysis is subject to acid or base epimerization to produce the desired compound of formula (III). Preferred acids include HCl, HBr, trifluoroacetic acid, and sulfuric acid. Most preferred R and $R^1$ substituents are phenyl and substituted phenyl wherein the substituents are selected from the group consisting of $C_1$–$C_6$ alkyl, $C_1$–$C_6$ alkoxy, $C_1$–$C_6$ alkylthio, $C_1$, phenyl, and phenyl(alkyl).

In another embodiment of this invention there is provided pharmaceutical formulations comprising as an active ingredient an effective amount of a compound of Formula I or II and a pharmaceutically acceptable carrier, excipient or diluent therefor. Such formulations can be prepared for oral or parenteral administration for the treatment and prevention of disorders of the gastrointestinal, central nervous and appetite regulatory systems of warm-blooded vertebrates, especially a man. The formulations are particularly useful for the treatment of 1) neuroleptic related extrapyramidal motor syndromes, 2) benzodiazepine cessation and withdrawal, 3) psychosis, 4) anxiety, 5) nicotine cessation and withdrawal, 6) smoking cessation, 7) for the inhibition of colonic motility and 8) neoplasms of gastrointestinal origin.

For oral use of an antagonist of CCK or gastrin of this invention, the selected compound can be administered, for example, in the form of tablets or capsules, or as an aqueous solution or suspension. In the case of tablets, common excipients include binding agents, for example, syrup, acacia, gelatin, sorbitol, tragacanth, polyvinylpyrrolidine (Povidone), methylcellulose, ethylcellulose, sodium carboxymethylcellulose, hydroxypropylmethylcellulose, sucrose and starch; fillers and carriers, for example, corn starch, gelatin, lactose, sucrose, microcrystalline cellulose, kaolin, mannitol, dicalcium phosphate, sodium chloride and alginic acid; lubricants such as magnesium stearate; disintegrants such as croscarmellose, microcrystalline cellulose, corn starch, sodium starch glycolate and alginic acid; and suitable wetting agents such as lauryl sulfate. For oral administration in capsule form, useful diluents include lactose and dried corn starch. When aqueous suspensions are desirable for oral use, the active ingredient can be combined with emulsifying and suspending agents, for example, sorbitol, methylcellulose, glucose/sugar syrup, gelatin, hydroxyethylcellulose, carboxymethylcellulose, aluminum stearate gel or hydrogenated edible oils, for example, almond oil, fractionated coconut oil, oily esters, propylene glycol or ethyl alcohol; flavoring agents such as peppermint, oil of wintergreen, cherry flavoring or the like; and preservatives such as methyl or propyl phydroxybenzoates or ascorbic acid.

The pharmaceutical formulations can also be prepared for parenteral use. Such formulations typically take the form of sterile isotonic solutions of the active ingredient according to standard pharmaceutical practice.

Depending on the method of administration, the formulations may be prepared as tablets, granules, gum, mist, capsules, depot formulation, injection solutions for parenteral use, gel or suspension for transdermal delivery, suspensions or elixirs for oral use or suppositories. The formulations of the invention may, if desired, be prepared so as to provide quick, sustained or delayed release of the active ingredient after administration to the patient. Preferably the formulations are prepared in a dosage unit form, each dosage containing from 0.05 to about 50 mg, more usually 1 to about 20 mg, of the active ingredient. The appropriate dose of the compound of the present invention for its use as an antagonist of CCK or gastrin in humans will vary according to the age, weight and response of the individual patient, as well as the severity of the patient symptoms and the nature of the condition being treated. Thus, the preferred daily dose will normally be determined by the prescribing physician. However, in most instances, effective daily doses of the compounds of this invention will range from about 0.05 mg to about 50 mg/kg and preferably about 0.5 mg to about 20 mg/kg in a single or divided doses.

The following Examples are provided to describe further the compounds of this invention and methods for their preparation.

Tetrahydrofuran (THF) was dried by distillation from sodium/benzophenone. Reactions and workup steps were conducted at room temperature unless otherwise noted. Solvents were removed using a rotary evaporator at reduced pressure. Chromatography was performed on normal-phase silica columns except as noted. Titrations were performed in 2:1 DMF:$H_2O$ as solvent.

EXAMPLE 1

1-[(4-Chloro-3-trifluoromethylphenyl)aminocarbonyl]-4,5-diphenyl-3-pyrazolidinone [Method A]

4,5-Diphenyl-3-pyrazolidinone (3.00 g, 12.6 mmol) was dissolved in 40 mL THF under nitrogen, then a solution of 4-chloro-3-trifluoromethylphenylisocyanate (2.87 g, 13.0 mmol, 1.03 eq.) in 10 mL THF added over 2 min. After 2.3 hr, solvent was removed in vacuo, and the residue triturated with 25 mL toluene. The resulting solid was pulverized, washed twice with toluene, and dried in vacuo at 65° C. to give 4.94 g (85%) white solid.

¹H NMR (d₆-DMSO) δ 3.81 (br s, 1H), 5.56 (br s, 1H), 7.26–7.50 (m, 10H), 7.62 (d, J=9 Hz, 1H), 7.89 (dd, J=3, 9 Hz, 1H), 8.13 (br s, 1H), 9.64 (br s, 1H), 10.90 (br s, 1H); mass spectra (MS) 460 (M+1+);

Analysis for $C_{23}H_{17}ClF_3N_3O_2$: Calc.: C, 60.07; H, 3.73; N, 9.14; Found: C, 59.99; H, 3.60; N, 8.89.

EXAMPLE 2

1-[(4-N,N-Dimethylaminophenyl)aminocarbonyl]-4,5-diphenyl-3-pyrazolidinone [Method B]

4-N,N-Dimethylaminoaniline (2.00 g, 14.68 mmol) and triethylamine (3.63 g, 35.87 mmol, 2.44 eq.) were dissolved in 50 mL toluene under nitrogen, then triphosgene (1.45 g, 4.89 mmol, 0.333 eq.) added in one batch as a neat solid. The mixture was heated to reflux for 2.5 hr, cooled, then quickly filtered, the collected solid washed twice with toluene, and the combined filtrates evaporated in vacuo to give crude 4-N,N-dimethylaminophenylisocyanate as 2.57 g brown oil. This was redissolved in 50 mL THF and a solution of 4,5-diphenyl-3-pyrazolidinone (3.50 g, 14.69 mmol, 1.00 eq.) in 50 mL THF added over 3 min. After 20.7 hr, solvent was removed in vacuo and the product isolated by chromatography (preparative HPLC; 0–50% EtOAc:toluene gradient) as 1.73 g yellow oil which slowly crystallized. Recrystallization from toluene gave 744 mg (13%) white crystalline solid:

¹H NMR (d₆-DMSO) δ 2.84 (s, 6H), 3.71 (s, 1H), 5.55 (s, 1H), 6.67 (d, J=8 Hz, 2H), 7.12–7.52 (m, 12H), 8.86 (br s, 1H), 10.70 (br s, 1H); MS 400 (M+) ; titration p$K_a$'s 4.0, 7.9.

Analysis for $C_{24}H_{24}N_4O_2$: Calc.: C, 71.98, H, 6.04, N, 13.99;

Found: C, 72.08, H, 6.06, N, 14.06.

EXAMPLE 3

1-[(4-Benzyloxyphenyl)aminocarbonyl]-4,5-diphenyl-3-pyrazolidinone [Method C]

4-Benzyloxybenzoic acid (2.0 g, 8.8 mmol was suspended in 50 mL toluene with oxalyl chloride (5 mL) and heated to reflux for 15 min. Solvent was removed in vacuo, the residue redissolved in 30 mL acetone, and an aqueous solution of NaN₃ (1.16 g, 17.6 mmol, 2.0 eq. in 10 mL H₂O) added dropwise with external cooling by a water bath. The mixture was stirred for 1 hour, diluted with H₂O, extracted twice with toluene, then the combined extracts washed with water and brine, and dried over Na₂SO₄. This solution of acyl azide was treated with 4,5-diphenyl-3-pyrazolidinone (1.6 g, 6.8 mmol, 0.76 eq.), warmed until bubbles evolved, and heating maintained for 30 min. After stirring overnight at room temperature, the solvent was removed in vacuo, and the product isolated by chromatography (0–30% EtOAc:hexane gradient) as 1.6 g (52%) white solid: mp 127°–30° C.;

¹H NMR (CDCl₃) δ 3.95 (d, J=6 Hz, 1H), 5.0 (s, 2H), 5.55 (d, J=6 Hz, 1H), 6.8 (d, J=10 Hz, 2H), 6.86–7.46 (m, 16H), 7.05 (d, J=10 Hz, 2H), 8.95 (s, 1H); MS 463 (M+); titration p$K_a$ 7.7.

Analysis for $C_{29}H_{25}N_3O_3$: Calc.: C, 75.14; H, 5.44; N, 9.07; Found: C, 75.15; H, 5.49; N, 9.14.

EXAMPLE 4

1-[(2-[1,2,3,4-Tetrahydronaphthyl])aminocarbonyl]-4,5-diphenyl-3-pyrazolidinone [Method D]

1,2,3,4-Tetrahydro-2-naphthoic acid (639 mg, 3.63 mmol) was dissolved in 80 mL benzene under nitrogen, azeotropically dried by distilling a small portion of the solvent, then diphenylphosphorylazide (1.12 g, 4.08 mmol, 1.1 eq.) and Et₃N (0.41 g, 4.02 mmol, 1.1 eq.) added and the mixture heated to reflux for 1 hour. Solvent was removed in vacuo, the residue dissolved in dry THF under nitrogen, and 4,5-diphenyl-3-pyrazolidinone (784 mg, 3.29 mmol, 0.91 eq.) added and the mixture stirred overnight. The solvent was removed in vacuo and the product isolated by chromatography (25–50% EtOAc:hexane gradient) as 0.92 g (68%) white foam. Recrystallization of a 120 mg sample from i-Pr₂O:i-PrOH gave 94 mg white solid, containing a 1:1 mixture of two diastereomers by NMR: mp 82°–95° C.;

¹H NMR (CDCl₃) d 1.46–1.66 (m, 1H), 1.79–1.97 (m, 1H), 2.30–2.84 (m, 2H), 2.95 (apparent t of d, J=6, 16 Hz, 1H), 3.87 (apparent d, J=6 Hz, 1H) , 4.09 (m, 1H) , 5.12 (m, 1H) , 5.34 (apparent d of d, J=6, 14 Hz, 1H), 6.86–7.40 (m, 14 H), c. 9.0 (v br s, 1H);MS 411 (M+).

Analysis for $C_{26}H_{25}N_3O_2$: Calc.: C, 75.89; H, 6.12; N, 10.21; Found: C, 75.75; H, 6.32; N, 9.72.

EXAMPLE 5

1-[(3-Trifluoromethylbenzoyl]-4,5-diphenyl-3-pyrazolidinone [Method E]

A solution of 4,5-diphenyl-3-pyrazolidinone (2.0 g, 8.4 mmol) in 50 mL CH₂Cl₂ and 5 mL pyridine was treated dropwise with a solution of 3-trifluoromethylbenzoylchloride (1.4 g, 8.4 mmol) in 25 mL CH₂Cl₂ and stirred overnight. The mixture was washed with 1N HCl, dried over Na₂SO₄, evaporated, and the product isolated by chromatography (preparative HPLC) as 840 mg (24%) purple foam:

¹H NMR (CDCl₃) δ 3.83 (s, 1H), 5.16 (s, 1H), 7.2–7.64 (m, 15H); MS 410 (M+); titration p$K_a$ 7.15.

Analysis for $C_{23}H_{17}F_3N_2O_2$: Calc.: C, 67.31; H, 4.18; N, 6.83; Found: C, 67.52; H, 4.18; N, 6.66.

EXAMPLE 6

1-[(4-Chlorophenyl)oxycarbonyl]-4,5-diphenyl-3pyrazolidinone [Method F]

A solution of 4,5-diphenyl-3-pyrazolidinone (1.25 g, 5.26 mmol) in 50 mL CHCl₃ was treated with a solution of 4-chlorophenylchloroformate (1.0 g, 5.26 mmol) in 10 mL CHCl₃ and stirred overnight. The solvent was removed in vacuo and the residue recrystallized from EtOAc:hexane to give 1.6 g (58%) white solid: mp 175°–7° C.

¹H NMR (CDCl₃) δ 3.98 (d, J=6 Hz, 1H), 5.62 (d, J=6 Hz, 1H), 6.8–7.5 (m, 15H); MS 392 (M+); titration p$K_a$ 7.8.

Analysis for $C_{22}H_{17}Cl_1N_2O_3$: Calc.: C, 67.2 6; H, 4.3 6; N, 7.13; Found: C, 67.49, H, 4.54, N, 7.17.

EXAMPLE 7

1-[(3,4-Dichlorobenzyl)aminocarbonyl]-4,5-diphenyl-3pyrazolidinone [Method M]

A solution of 1-[(4-nitrophenyl)oxycarbonyl]4,5-diphenyl-3-pyrazolidinone (1.00 g, 2.48 mmol) and 3,4-dichlorobenzylamine (5 mL) in 50 mL abs. EtOH was heated to reflux for 8 hours. Solvent was removed in vacuo, the residue taken up in CH₂Cl₂, washed twice with 1N HCl and once with pH 7 buffer, and dried over Na₂SO₄. After removal of solvent in vacuo, the product was purified by chromatography (0–35% EtOAc:hexane gradient) to give 250 mg (23%) solid:

¹H NMR (CDCl₃) δ 3.93 (d, J=6 Hz, 1H), 4.28 (dABq, J=7, 15 (JAB) Hz, Δυ=48 Hz, 2H), 5.50 (d, J=6 Hz, 1H), 5.56 (br t, J=7 Hz, 1H), 6.92-7.44 (m, 13H), 8.73 (br s, 1H); MS 439 (M+); titration pK$_a$ 8.4.

Analysis for C₂₃H₁₉Cl₂N₃O₂: Calc.: C, 62.74; H, 4.35; N, 9.54; Found: C, 62.49; H, 4.53; N, 9.25.

EXAMPLE 8

2-[(4-Chloro-3-trifluoromethylphenyl)amino-carbonyl]-4,5-diphenyl-3-pyrazolidinone [Method N]

1-[(4-Chloro-3-trifluoromethylphenyl)aminocarbonyl]-4,5-diphenyl-3-pyrazolidinone (2.00 g, 4.35 mmol) in 100 mL toluene was heated at reflux for 24 hours. After removal of solvent in vacuo, the rearranged product was isolated by chromatography (CH₂Cl₂), then recrystallized from i-Pr₂O:hexane, to give 300 mg (15%) white solid: mp 72°-4° C.

¹H NMR (CDCl₃) δ 4.22 (d, J=12 Hz, 1H), 4.82 (dd, J=9,12 Hz, 1H), 5.44 (d, J=9 Hz, 1H), 7.20 (m, 2H), 7.32 7.42 (m, 8H), 7.46 (d, J=9 Hz, 1H), 7.72 (dd, J=3, 9 Hz, 1H), 7.87 (d, J=3 Hz, 1H), 10.56 (br s, 1H); MS 459 (M+).

Analysis for C₂₃H₁₇ClF₃N₃O₂: Calc.: C, 60.07; H, 3.73; N, 9.14; Found: C, 59.95; H, 3.92; N, 8.88.

EXAMPLE 9

1-[6-Chloro-2-benzothiazolyl]-4,5-diphenyl-3-pyrazolidinone [Method O]

The reaction was conducted under a dry nitrogen atmosphere. A suspension of 4,5-diphenyl-3-pyrazolidinone (1.19 g, 5.00 mmol) in 35 mL toluene was treated with 0.40 g NaH (60% in mineral oil; hydride content 0.24 g, 10.0 mmol, 2.00 eq.), and the mixture stirred at 45° C. for 2 hours. 2,6-Dichlorobenzothiazole (1.02 g, 5.00 mmol, 1.00 eq.) was added and stirring continued at 80° C. for 20 hours. After cooling, the reaction mixture was poured onto 30 mL ice-cooled 0.5 N HCl, extracted with EtOAc, and the separated organic phase washed twice with brine, dried over Na₂SO₄, and the solvent evaporated in vacuo. The residue was recrystallized from Et₂O:hexane to provide 1.46 g (72%) light tan crystals: mp 170.5°-2.5° C.

¹H NMR (CDCl₃) δ 4.07 (br d, J=6 Hz, 1H), 5.24 (br d, J=6 Hz, 1H), 7.16-7.58 (m, 14H);MS 405 (M+); titration pK$_a$ 6.60

Analysis for C₂₂H₁₆C₁N₃OS: Calc.: C, 65.10; H, 3.97; N, 10.35; Found: C, 64.85; H, 4.13; N, 10.12.

EXAMPLE 10

1-[(4-Aminophenyl)aminocarbonyl]-4,5-diphenyl-3-pyrazolidinone

1-[(4-Nitrophenyl)aminocarbonyl]-4,5-diphenyl-3-pyrazolidinone (500 mg, 1.24 mmol) was dissolved in 50 mL EtOH and hydrogenated with 5% Pd/C (500 mg) under 60 p.s.i. H₂, overnight at room temperature. The mixture was filtered to remove catalyst, solvent removed in vacuo, and the product isolated by chromatography (0-50% EtOAc:hexane gradient) as 125 mg (27%) solid.

¹H NMR (CDCl₃) δ 3.97 (d, J=6 Hz, 1H), 5.50 (d, J=6 Hz, 1H), 6.58 (d, J=10 Hz, 2H), 6.96 (d, J=10 Hz, 2H), 7.2-7.5 (m, 10H); MS 372 (M+); titration pK$_a$ 4.5, 8.1.

Analysis for C₂₂H₂₀N₄O₂: Calc.: C, 70.95; H, 5.41; N, 15.04; Found: C, 70.65; H, 5.42; N, 14.75.

EXAMPLE 11

1-[(4-Bromophenyl)aminocarbonyl]-2-(O-t-butylcarboxymethyl)-4,5-diphenyl-3-pyrazolidinone and 1-[(4-bromophenyl)aminocarbonyl]-3-(O-t-butylcarboxy-methoxy)-4,5-diphenyl-2-pyrazoline To a suspension of 1-[(4-bromophenyl)aminocarbonyl]-4,5-diphenyl-3-pyrazolidinone (2.0 g, 4.6 mmol) in 30 mL abs. EtOH were added a solution of KOH (1.1 eq.) in abs. EtOH and t-butyl bromoacetate (5 mL). After stirring for 3 days a precipitate of KBr had appeared. The mixture was diluted with H₂O, extracted with Et₂O, then the Et₂O layer washed with H₂O and brine, dried over Na₂SO₄, and evaporated in vacuo. An inseparable mixture of two products was isolated by chromatography (0-25% EtOAc:hexane gradient) as 1.3 g (52%) foam, containing a 3:2 ratio of N-alkylated to O-alkylated products [first and second title products, respectively] by NMR:

¹H NMR (CDCl₃) N-alkylated: δ 1.53 (s, 9H), 3.96 (d, J=19 Hz, 1H), 4.06 (s, 1H), 4.65 (d, J=19 Hz, 1H), 5.95 (s, 1H), 7.23-7 .46 (m, 14H), 9.70 (s, 1H); O-alkylated: δ1.53 (s, 9H), 4 .18 (d, J=7 Hz, 1H), 4.67 (s, 2H), 5.40 (d, J=7 Hz, 1H), 7 .23-7.46 (m, 14H), 7.74 (s, 1H); MS 549, 551 (M+'s for Br isotopes ) .

Analysis for C₂₈H₂₈BrN₃O₄: Calc.: C, 61.10; H, 5.13; N, 7.63; Found: C, 60.94, H, 4.93; N, 7.85.

EXAMPLE 12

1-[(4-Bromophenyl)aminocarbonyl]-2-carboxymethyl-4,5-diphenyl-3-pyrazolidinone and 1-[(4-bromophenyl)aminocarbonyl]-3-carboxymethoxy-4,5-diphenyl-2-pyrazoline The regioisomeric mixture of t-butyl esters from Example 11 [c. 3:2 mixture of N- to O-alkylated] (500 mg, 0.91 mmol) was dissolved in 30 mL CH₂Cl₂ and 5 mL trifluoroacetic acid. After 4 hours TLC (CH₂Cl₂) indicated disappearance of starting materials. Solvent was removed in vacuo and a mixture of two products isolated by chromatography (0-100% EtOAc:hexane gradient) as 180 mg (40%) foam, comprised of a 4:3 ratio of N-alkylated to O-alkylated compounds [first and second title products, respectively] by NMR.

¹H NMR (CDCl₃) N-alkylated: δ 4.09 (d, J=2 Hz, 1H), 4.10 (d, J=19 Hz, 1H), 4.68 (d, J=19 Hz, 1H), 5.83 (d, J=2 Hz, 1H), 7.20-7.50 (m, 14H), 9.08 (s, 1H); O-alkylated: δ 4.19 (d, J=5 Hz, 1H), 4.83 (ABq, J=16 Hz, Δυ=30 Hz, 2H), 5.46 (d, J=5 Hz, 1H), 7.20-7.50 (m, 14H), 7.75 (s, 1H); MS 493, 495 (M+s for Br isotopes); titration pK$_a$ 4.8.

Analysis for C₂₄H₂₀BrN₃O₄: Calc.: C, 58.31; H, 4.08; N, 8.50; Found: C, 58.59; H, 4.03; N, 8.24.

The N- and O-alkylated products were separated by chromatography on a Waters C₁₈ reverse-phase column, using 30-40% CH₃CN:H₂O buffered with 0.3-0.5% NH₄OAC. The leading fractions from the first pass were evaporated, lyophilized, then taken up in CH₂Cl₂, washed twice with 1 N HCl, and the solvent removed in vacuo to provide 28 mg O-alkylated product:

¹H NMR (CDCl₃ δ 4.19 (d, J=7 Hz, 1H), 4.84 (ABq, J=17 Hz, Δυ=25 Hz, 2H), 5.45 (d, J=7 Hz, 1H), 6.39 (br s, 1H), 7.20-7.40 (m, 14H), 7.70 (s, 1H).

The later fractions were rechromatographed twice more, then similarly processed to give 8 mg N-alkylated product:

¹H NMR (CDCl₃) δ CDCl₃ 4.05 (s, 1H), 4.08 (br d, J=18 Hz, 1H), 4.70 (br d, J=18 Hz, 1H), 5.82 (s, 1H), 7.21 7.50 (m, 14H), 9.0 (br s, 1H).

EXAMPLE 13

1-[(4-Trifluoromethylphenyl)aminocarbonyl]-3-methoxy-4,5diphenyl-2-pyrazoline

A solution of 1-[(4-trifluoromethylphenyl)-aminocarbonyl] -4,5-diphenyl-3-pyrazolidinone (740 mg, 1.74 mmol) and KOH (122 mg of 88% pure, 1.1 eq.) in 30 mL abs. EtOH was treated with iodomethane (5 mL) and stirred overnight. The mixture was diluted with H₂O, extracted twice with CH₂Cl₂, and the combined extracts washed with H₂O, dried over Na₂SO₄, and evaporated in vacuo. The product was isolated by chromatography (0-15% EtOAc:hexane gradient) as 61 mg (8%) solid.

¹H NMR (CDCl₃) δ 4.0 (s, 3H), 4.11 (d, J=6 Hz, 1H), 5.48 (d, J=6 Mz, 1H), 7.2-7.74 (m, 14H), 8.09 (s, 1H); MS 439 (H+).

Also isolated was 1-[(4-trifluoromethylphenyl)aminocarbonyl]-2-methyl-4,5-diphenyl-3-pyrazolidinone, corresponding to a product prepared, according to the method of Example 1, from 2-methyl-4,5-diphenyl-3pyrazolidinone and 4-trifluoromethylphenylisocyanate.

EXAMPLE 14

1-(Indole-2-carbonyl)-4,5-diphenyl-3-pyrazolidinone

Indole-2-carboxylic acid (1.35 g, 8.38 mmol), oxalyl chloride (4 mL), and DMF (3 drops) were added in order to 50 mL toluene, and stirred until gas evolution subsided and a homogeneous solution was obtained (c.20 min). Solvent was removed in vacuo, the residue taken up in CH₂Cl₂, and added to a solution of 4,5-diphenyl-3pyrazolidinone (2.0 g, 8.40 mmol, 1.00 eq.) in 50 mL CH₂Cl₂ and 5 mL pyridine. After stirring overnight, the solution was washed with 1N HCl, dried over Na₂SO₄, and solvent removed in vacuo. The residual solid was stirred with CH₂Cl₂, filtered, and recrystallized from DMF:H₂O to give 1.42 g 44%) white solid: mp 248°-50° C.

¹H NMR (d₆-DMSO) δ 3.82 (s, 1H), 5.86 (s, 1H), 6.95-7.6 (m, 16H , 11.84 (br s, 1H); MS 381 (M+) ; titration PK$_a$ 6.75.

Analysis for C₂₄H₁₉N₃O₂: Calc.: C, 75.57; H, 5.02; N, 11.02; Found: C, 75.38, H, 5.21; N, 10.99.

Examples 15-135 are summarized below in Table I. The compound of each Example is identified by reference to the structural formula preceeding each group of Examples. The method for preparing each compound is indicated by reference to the Methods A-O, corresponding to the procedures identified in the foregoing Examples 1-9. Example 133A, and Examples 137-138 in Table II follow the same format. Examples 136, 139A/139B, 140-143 are illustrated separately to show physical chemistry data as well as the individual methods of preparation of these compounds. The phenyl groups on the pyrazolidinone ring of the compounds of Examples 1-67, 74-109, and 136-143 are in the trans position.

TABLE I
PHYSICAL CHEMISTRY DATA ON CCK/GASTRIN ANTAGONISTS

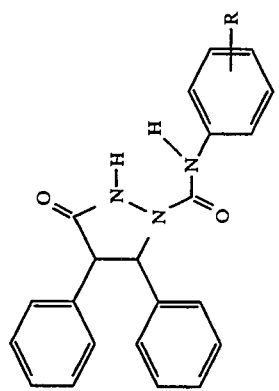

Structure for examples 15-59 below

| Ex. | R | Method of Prep. | Solvent of Cryst.[a] | Yield % | Mp, °C. | MS | 1HNMR | Formula | Analysis, % Theory/Found C | H | N |
|---|---|---|---|---|---|---|---|---|---|---|---|
| 15 | H | A | EtOAc: hexane | 2.20 g 73% | 168-70 | 357 (M+) | DMSO 3.75(s, 1H), 5.58(s, 1H), 6.96-7.53(m, 15H), 9.16(s, 1H), 10.8(s, 1H) | C22H19N3O2 | 73.93 73.84 | 5.36 5.42 | 11.76 11.75 |
| 16 | 4-CF3 | A (THF) | PhMe | 2.32 g 43.3% | 189-91 | 426(M+1) | DMSO 3.80(brs, 1H), 5.58(brs, 1H), 7.30-7.80(m, 14H), 9.54(brs, 1H), 10.90(brs, 1H) | C23H18F3N3O2 | 64.94 64.67 | 4.26 4.09 | 9.88 9.75 |
| 17 | 4-F | A | EtOAc: hexane | 1.76 g 65% | 189-91 | 375(M+) | CDCl3 3.99(d, J=6Hz, 1H), 5.53 (d, J=6Hz, 1H), 6.85-7.5(m, 14H) 8.95(brs, 1H) | C22H18FN3O2 | 70.37 70.24 | 4.83 4.85 | 11.17 11.09 |
| 18 | 4-Cl | A | EtOAc: hexane | 2.44 g 48% | 173-5 | 391(M+) | DMSO 3.78(s, 1H), 5.56(s, 1H), 7.24-7.6(m, 14H), 9.32(s, 1H), 10.81(s, 1H) | C22H18ClN3O2 | 67.43 67.30 | 4.63 4.79 | 10.72 10.67 |
| 19 | 4-Cl (N—Me) | B | chrom (prep plates) | 60 mg 40% | | 405(M+) | CDCl3 3.18(s, 3H), 3.53(d, J=3 Hz, 1H), 4.86(d, J=3Hz, 1H), 6.9-7.42(m, 15H) | C23H20ClN3O2 | | | |
| 20 | 4-Br | A (THF) | PhMe (to give PhMe hemisolvate) | 2.64 g 58% | 174-6[b] | 435, 437 (M+'s for Br Isotopes) | DMSO 3.77(brs, 1H), 5.57(brs, 1H), 7.12-7.55(m, 14H), 9.31(brs, 1H), 10.81(brs, 1H) | C22H18BrN3O2·½(C7H8) | 63.49 63.15 | 4.60 4.60 | 8.71 8.81 |
| 21 | 4-I | C | EtOAc: hexane | 90 mg 2% | 177-9 | 483(M+) | CDCl3 4.0(d, J=6Hz, 1H), 5.54(d, J=6Hz, 1H), 6.9-7.5(m, 14H) | C22H18IN3O2 | 54.67 54.46 | 3.75 3.70 | 8.69 8.51 |
| 22 | 4-CO2Et | A | chrom | 480 mg 11% | | 430(M+1) | CDCl3 1.38(t, J=9Hz, 3H), 4.02 (d, J=6Hz, 1H), 4.34(q, J=8Hz, 2H), 5.56(d, J=6Hz, 1H), 7.18-7.95(m, 14H) | C25H23N3O4 | | | |
| 23 | 4-COMe | A | chrom | 31 mg 1.2% | | 399(M+) | CDCl3 2.52(s, 3H), 4.03(d, J=6 Hz, 1H), 5.55(d, J=6Hz, 1H), 7.31 (d, J=12Hz, 2H), 7.2-7.5(m, 11Hz), 7.83(d, J=12Hz, 2H), 9.18(brs, 1H) | | | | |
| 24 | 4-NO2 | A | EtOAc: hexane | 1.8 g 71% | 168-70 | 402(M+) | DMSO 3.83(s, 1H), 5.58(s, 1H), 7.25-7.5(m, 10H), 7.82(d, J=14 Hz, 2H), 8.2(d, J=14Hz, 2H), 9.77 1H) | C22H18N4O4 | 65.67 65.43 | 4.51 4.56 | 13.92 13.70 |

TABLE I-continued
PHYSICAL CHEMISTRY DATA ON CCK/GASTRIN ANTAGONISTS

| # | R | | | | | MS | NMR | Formula | C | H | N |
|---|---|---|---|---|---|---|---|---|---|---|---|
| 25 | 4-Me | A | PhMe | 1.72 g 44% | | 371(M+) | DMSO 2.25(s, 3H), 3.75(s, 1H), 5.57(brs, 1H), 7.08(d, J=8Hz, 2H), 7.3–7.5(m, 12H), 9.03(brs, 1H), 10.74(brs, 1H) | C23H21N3O2 | 74.37 74.52 | 5.70 5.50 | 11.31 11.10 |
| 26 | 4-Et | A | triturated with PhMe | 3.74 g 92% | | 385(M+) | DMSO 1.16(t, J=8Hz, 3H), 2.55 (q, J=8Hz, 2H), 3.74(brs, 1H), 5.57(brs, 1H), 7.12(d, J=9Hz, 2H), 7.14–7.54(m, 12H), 9.06(brs, 1H), 10.76(brs, 1H) | C24H23N3O2 | 74.78 75.00 | 6.01 6.13 | 10.90 10.71 |
| 27 | 4-n-Pr | C | EtOAc: hexane | 230 mg 6% | 169–71 | 400(M+1) | CDCl3 0.9(t, J=10Hz, 3H), 1.58 (m, 2H), 2.5(t, J=10Hz, 2H), 4.0 (d, J=6Hz, 1H), 5.54(d, J=6Hz, 1H), 6.82(s, 1H), 7.03(d, J=12Hz, 2H), 7.1(d, J=12Hz, 2H), 7.23–7.5 (m, 10H), 8.62(brs, 1H) | C25H25N3O2 | 75.16 75.07 | 6.31 6.23 | 10.52 10.50 |
| 28 | 4-n-Bu | A | EtOAc: hexane | 1.22 g 47% | 165–7 | 413(M+) | CDCl3 0.95(t, J=10Hz, 3H), 1.3 (m, 2H), 1.5(m, 2H), 2.56(t, J=10 Hz, 2H), 3.96(d, J=6Hz, 1H), 5.54 (d, J=6Hz, 1H), 6.93(s, 1H), 7.30 (d, J=12Hz, 2H), 7.1(d, J=12Hz, 2H), 7.23–7.46(m, 10H), 9.04(s, 1H) | C26H27N3O2 | 75.52 75.23 | 6.58 6.35 | 10.16 9.97 |
| 29 | 4-i-Pr | A | THF: EtOAc | 1.0 g 40% | 191–3 | 399(M+) | CDCl3 1.21(d, J=10Hz, 6H), 2.83 (m, J=10Hz, 1H), 4.0(d, J=6Hz, 1H), 5.53(d, J=6Hz, 1H), 6.83(s, 1H), 7.1–7.5(m, 14H), 8.65(s, 1H) | C25H25N3O2 | 75.16 75.37 | 6.31 6.42 | 10.52 10.46 |
| 30 | 4-t-Bu | C | EtOAc | 790 mg 30% | 204–7 | 413(M+) | CDCl3 1.26(s, 9H), 4.0(d, J=6Hz, 1H), 5.50(d, J=6Hz, 1H), 6.83(s, 1H), 7.12(d, J=12Hz, 2H), 7.35(d, J=12Hz, 2H), 7.2–7.44(m, 10H), 8.6(s, 1H) | C26H27N3O2 | 75.52 75.74 | 6.58 6.78 | 10.16 10.18 |
| 31 | 4-c-Hexyl | B | chrom, then EtOAc, then chrom | 104 mg 3% | 200–3 | 439(M+) | DMSO 1.15–1.85(m, 10H), 2.22 (m, 1H), 3.74(s, 1H), 5.58(s, 1H), 7.13(d, J=12Hz, 1H), 7.46(d, J=12Hz, 1H), 7.3–7.43(m, 10H), 9.08(s, 1H), 10.76(s, 1H) | C28H29N3O2 | 76.51 76.29 | 6.65 6.81 | 9.56 9.38 |
| 32 | 4-Ph | C | chrom, then, EtOAc: hexane | 312 mg 17% | 180–2 | 433(M+) | CDCl3 4.02(d, J=6Hz, 1H), 5.60 (d, J=6Hz, 1H), 7.2–7.56(m, 20H), 9.4(brs, 1H) | C28H23N3O2 | 76.94 75.86 | 5.50 5.39 | 9.97 9.96 |
| 33 | 4-OMe | A | EtOAc: hexane | 1.9 g 79% | 154–7 | 387(M+) | CDCl3 3.74(s, 3H), 3.96(d, J=6 Hz, 1H), 5.53(d, J=6Hz, 1H), 6.74 (d, J=12Hz, 2H), 7.15(d, J=12Hz, 2H), 6.9–7.43(m, 11H), 9.0(brs, 1H) | C23H21N3O3 | 71.30 70.71 | 5.46 5.67 | 10.85 10.71 |
| 34 | 4-OEt | A | triturated with PhMe | 2.93 g 87% | | 401(M+) | DMSO 1.31(t, J=7Hz, 3H), 3.73 (s, 1H), 3.97(q, J=7Hz, 2H), 5.55 (brs, 1H), 6.84(d, J=8Hz, 2H), 7.3–7.53(m, 12H), 8.99(brs, 1H), 10.72(brs, 1H) | C24H23N3O3 | 71.80 72.05 | 5.77 5.89 | 10.47 10.21 |
| 35 | 4-O-t-Br | B | triturated | 1.34 g | 178–80 | 415(M+) | CDCl3 1.27(d, J=8Hz, 6H), 3.93 | C25H25N3O3 | 72.27 | 6.06 | 10.11 |

5,399,565

TABLE I-continued

PHYSICAL CHEMISTRY DATA ON CCK/GASTRIN ANTAGONISTS

| # | R | Method | Solvent | Yield | mp | MS | NMR | Formula | C | H | N |
|---|---|---|---|---|---|---|---|---|---|---|---|
| | | | with Et2O | 74% | | | (d, J=5Hz, 1H), 4.42(septet, J=6 Hz, 1H), 5.54(d, J=6Hz, 1H), 6.72 (d, J=9Hz, 2H), 6.95(s, 1H), 7.05 (d, J=9Hz, 2H), 7.13-7.39(m, 11H) | | 72.25 | 6.04 | 10.06 |
| 36 | 4-OCH2CH2Ph | B | chrom (EtOAc: hexane), then triturated with PhMe | 324 mg 31% | | 477(M+) | DMSO 3.01(t, J=7Hz, 2H), 3.73 (s, 1H), 4.14(t, J=7Hz, 2H), 5.55 (brs, 1H), 6.85(d, J=9Hz, 2H), 7.18-7.52(m, 17H), 9.01(brs, 1H), 10.72(brs, 1H) | C30H27N3O3 | 75.45 75.71 | 5.70 5.78 | 8.80 8.67 |
| 37 | 4-OPh | A | EtOAc: CH3OH | 2.9 g 68% | 188-90 | 450(M+1) | DMSO 3.75(s, 1H), 5.59(s, 1H), 6.95-7.56(m, 19H), 9.21(s, 1H), 10.8(s, 1H) | C28H23N3O3 | 74.82 74.58 | 5.16 5.22 | 9.35 9.34 |
| 38 | 4-SMe | A | EtOAc: hexane | 1.6 g 65% | 160-2 | 403(M+) | CDCl3 2.42(s, 3H), 4.0(d, J=6Hz, 1H), 5.54(d, J=6Hz, 1H), 6.95-7.44(m, 15H), 8.98(brs, 1H) | C23H21N3O2S | 68.46 68.28 | 5.25 5.28 | 10.41 10.25 |
| 39 | 3-CF3 | A | EtOAc: hexane | 3.0 g 83% | 165-7 | 425(M+) | DMSO 3.8(s, 1H), 5.58(s, 1H), 7.3-7.56(m, 12H), 7.82(d, 1H), 7.98(s, 1H), 9.54(s, 1H), 10.88(s, 1H) | C23H18F3N3O2 | 64.94 65,07 | 4.27 4.19 | 9.88 9.77 |
| 40 | 3-NO2 | A | EtOAc: hexane | 2.11 g 84% | 164-6 | (no M+) | CDCl3 4.03(d, J=6Hz, 1H), 5.62 (d, J=6Hz, 1H), 7.2-8.1(m, 14H) | C22H19N4O4 | 65.57 | 4.51 | 13.92 |
| 41 | 3-Me | A | EtOAc: CH3OH | 1.05 g 46% | 188-90 | 371(M+) | DMSO 3.3(s, 3H), 3.74(s, 1H), 5.57(s, 1H), 6.8-7.54(m, 12H), 9.04(s, 1H), 10.86(s, 1H) | C23H21N3O2 | 74.37 74.17 | 5.70 5.63 | 11.31 11.04 |
| 42 | 3-OMe | A | EtOAc: hexane | 2.1 g 51% | 163-5 | 387(M+) | CDCl3 3.7(s, 3H), 3.98(d, J=6Hz, 1H), 5.54(d, J=6Hz, 1H), 6.56-7.48(m, 16H) | C23H21N3O3 | 71.30 71.29 | 5.46 5.72 | 10.85 10.59 |
| 43 | 3-O-i-Pr | B | C6H6: hexane | 450 mg 22% | 80-85 | 415(M+) | CDCl3 1.26(d, J=6Hz, 6H), 3.96 (d, J=5Hz, 1H), 4.45(septet, J=6 Hz, 1H), 5.51(d, J=5Hz, 1H), 6.54-6.62(m, 2H), 6.91-7.08(m, 3H), 7.21-7.50(m, 11H) | C25H25N3O3 | 72.27 71.99 | 6.06 6.18 | 10.11 9.94 |
| 44 | 3-OCH2Ph | B | triturated with Et2O | 1.64 g 85% | 143-44.5 | 463(M+) | CDCl3 3.99(d, J=5Hz, 1H), 4.97 (s, 2H), 5.54(d, J=5Hz, 1H), 6.66-6.68(m, 2H), 7.06(s, 1H), 7.09-7.12(m, 2H), 7.23-7.44(m, 16H) | C29H25N3O3 | 75.14 75.01 | 5.44 5.49 | 9.07 8.84 |
| 45 | 3-CF3, 4-Br | B | chrom | 120 mg 12% | | 503, 505 (M+'s for Br Isotopes) | CDCl3 4.03(d, J=6Hz, 1H), 5.58 (d, J=6Hz, 1H), 7.2-7.56(m, 15H) | C23H17BrF3N3O2 | 54.78 55.05 | 3.40 3.51 | 8.33 8.07 |
| 46 | 3,4-diCl | A | EtOAc: hexane | 2.2 g 49% | 169-71 | 425(M+) | CDCl3 4.04(d, J=6Hz, 1H), 5.57 (d, J=6Hz, 1H), 6.97-7.5(m, 15H) | C22H17Cl2N3O2 | 61.99 62.22 | 4.02 4.11 | 9.86 9.75 |
| 47 | 3-Cl, 4-F | A | EtOAc: hexane | 2.0 g 84% | 174-6 | 409(M+) | CDCl3 4.0(d, J=6Hz, 1H), 5.56(d, J=6Hz, 1H), 6.95-7.5(m, 15H) | C22H17ClFN3O2 | 64.47 64.03 | 4.18 4.76 | 10.25 9.53 |
| 48 | 3-NO2, 4-Cl | A | EtOAc: hexane | 910 mg 41% | 149-51 | 436(M+) | CDCl3 4.03(d, J=6Hz, 1H), 5.58 (d, J=6Hz, 1H), 7.2-7.82(m, 14H), 9.3(s, 1H) | C22H17ClN4O4 | 60.49 60.23 | 3.92 4.03 | 12.83 12.79 |
| 49 | 3,4-(CH2)3 | B | EtOAc: hexane, then chrom (EtOAc: | 380 mg 12% | 179-81 | 397(M+) | DMSO 1.97(m, 2H), 2.8(m, 4H), 3.7(s, 1H), 5.58(s, 1H), 7.12-7.5 (m, 13H), 9.0(s, 1H), 10.75(s, 1H) | C25H23N3O2 | 75.55 75.67 | 5.83 5.95 | 10.57 10.46 |

TABLE I-continued
PHYSICAL CHEMISTRY DATA ON CCK/GASTRIN ANTAGONISTS

| # | R | | Solvent | Yield | mp (°C) | MS | NMR | Formula | C calc/found | H calc/found | N calc/found |
|---|---|---|---|---|---|---|---|---|---|---|---|
| 50 | 3,4-(CH2)4 | D | hexane), then EtOAc chrom (EtOAc:CH2Cl2), then Et2O:CH2Cl2 | 354 mg 20% | 177–8.5 | 411(M+) | CDCl3 1.74(t, J=3Hz, 4H), 2.66 (d, J=7Hz, 4H), 3.97(d, J=5Hz, 1H), 5.55(d, J=5Hz, 1H), 6.83–6.92(m, 3H), 6.98(s, 1H), 7.24–7.44(m, 10H), 9.06(brs, 1H) | C26H25N3O2 | 75.89 / 76.08 | 6.12 / 6.33 | 10.21 / 10.05 |
| 51 | 3,4-dlOMe | B | chrom | 640 mg 11% | | 481(M+) | CDCl3 3.74(s, 3H), 3.82(s, 3H), 3.97(d, J=6Hz, 1H), 5.58(d, J=6Hz, 1H), 6.53–7.5(m, 14H), 8.7(s, 1H) | C24H23N3O4 | 69.05 / 68.92 | 5.55 / 5.54 | 10.07 / 10.12 |
| 52 | 3,4-OCH2O | B | EtOAc | 390 mg 7% | 179–81 | 401(M+) | DMSO 3.73(s, 1H), 5.55(s, 1H), 5.97(s, 2H), 6.8–7.6(m, 13H), 9.05(s, 1H), 10.75(s, 1H) | C23H19N3O4 | 68.82 / 68.96 | 4.77 / 4.76 | 10.47 / 10.29 |
| 53 | 2-CF3 | A | EtOAc | 3.46 g 77% | 143–5 | 425(M+) | DMSO 3.8(s, 1H), 5.6(s, 1H), 7.2–7.75(m, 15H), 8.68(s, 1H), 10.95 (s, 1H) | C23H18F3N3O2 | 64.94 / 65.15 | 4.26 / 4.19 | 9.88 / 9.60 |
| 54 | 2,3-dlCl | A | THF: hexane | 3.9 g 70% | 191–3 | 425(M+) | DMSO 3.78(s, 1H), 5.54(s, 1H), 7.3–7.6(m, 13H), 8.88(s, 1H), 11.05(s, 1H) | C22H17Cl2N3O2 | 61.93 / 62.00 | 4.02 / 3.96 | 9.86 / 9.94 |
| 55 | 2,4-dlCl | A | EtOAc: hexane | 1.7 g 63% | 150–3 | 425(M+) | CDCl3 4.02(d, J=6Hz, 1H), 5.38 (d, J=6Hz, 1H), 7.15–7.5(m, 13H), 8.1(d, J=10Hz, 1H), 8.95(s, 1H) | C22H17Cl2N3O2 | 61.98 / 62.15 | 4.02 / 4.28 | 9.86 / 9.95 |
| 56 | 2,4-dlF | A | chrom | 800 mg 32% | | 393(M+) | CDCl3 4.03(d, J=6Hz, 1H), 5.43 (d, J=6Hz, 1H), 6.8(m, 2H), 6.91 (s, 1H), 7.2–7.5(m, 9H), 7.93(m, 1H), 8.8(brs, 1H) | C22H17F2N3O2 | | | |
| 57 | 2-Cl, 5-CF3 | A | EtOAc: hexane | 1.38 g 29% | 130–2 | 459(M+) | CDCl3 4.05(d, J=6Hz, 1H), 5.41 (d, J=6Hz, 1H), 72–7.5(m, 14H), 8.53(s, 1H) | C23H17ClF3N3O2 | 60.07 / 60.37 | 3.73 / 3.95 | 9.14 / 9.03 |
| 58 | 3,5-dlCF3 | A | chrom | 3.6 g 69% | | 493(M+) | CDCl3 4.03(d, J=6Hz, 1H), 5.62 (d, J=6Hz, 1H), 7.2–7.58(m, 13H), 7.75(s, 2H) | C24H17F6N3O2 | 58.42 / 58.59 | 3.47 / 3.75 | 8.52 / 8.69 |
| 59 | 3,5-dlCl | A | EtOAc: hexane | 800 mg 30% | 166–8 | 425(M+) | DMSO 3.82(s, 1H), 5.54(s, 1H), 7.2(s, 1H), 7.15–7.55(m, 10H), 7.71 (s, 2H), 9.5(s, 1H), 10.95(s, 1H) | C22H17Cl2N3O2 | 61.99 / 61.75 | 4.02 / 3.94 | 9.86 / 9.65 |

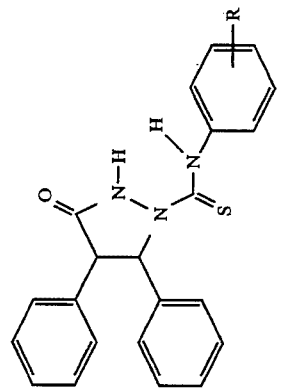

TABLE I-continued

PHYSICAL CHEMISTRY DATA ON CCK/GASTRIN ANTAGONISTS

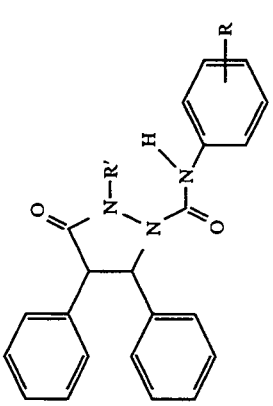

| Ex. | R | Method of Prep. | Solvent of Cryst.[a] | Yield, % | Mp, °C. | MS | 1HNMR | Formula | Analysis, % Theory/Found C | H | N |
|---|---|---|---|---|---|---|---|---|---|---|---|
| 60 | H | A (THF) | PhMe:hexane, then Et2O:hexane (to give Et2O solvate) | 117 mg 5% | 69-79 | 373(M+) | CDCl3 4.03(d, 1H), 5.77(d, 1H), 7.10-7.54(m, 16H), 9.6(brs, 1H) [plus for Et2O: 1.20(t, 6H), 3.48 (q, 4H)] | C22H19N3OS. C4H10O | 69.77 69.72 | 6.53 6.38 | 9.39 9.37 |
| 61 | 3-CF3 | A | chrom | 1.5 g 33% |  | 442(M+1) | CDCl3 4.07(d, J=6Hz, 1H), 5.82 (d, J=6Hz, 1H), 7.12-7.63(m, 16H) | C23H18F3N3OS | 62.58 6.87 | 4.11 4.22 | 9.52 9.34 |
| 62 | 4-CF3 | A | PhMe | 800 mg 29% | 87-90 | 441(M+), 442 (M+1) | CDCl3 4.09(d, J=6Hz, 1H), 5.77 (d, J=6Hz, 1H), 7.16(d, J=9Hz, 1H), 7.2-7.28(m, 3H), 7.3-7.44 (m, 7H), 7.44-7.64(m, 5H) | C23H18F3N3OS | 62.51 62.51 | 4.11 4.15 | 9.52 9.46 |
| 63 | 3-CF3, 4Cl | A | chrom, then triturated with hexane | 200 mg 10% | 80-2 | 475(M+), 476(M+1) | CDCl3 4.09(d, J=6Hz, 1H), 5.83 (d, J=6Hz, 1H), 7.06-7.6(m, 15H) | C23H17ClF3N3OS | 58.05 58.15 | 3.60 3.62 | 8.83 8.55 |
| 64 | 2,3-dlCl | A | EtOAC: hexane | 2.5 g 67% | 154-6 | 441(M+), 442, 444 (M+1's for Cl Isotopes) | DMSO 3.95(s, 1H), 6.16(s, 1H), 7.2-7.6(m, 13H), 9.5(brs, 1H) 11.5(brs, 1H) | C22H17Cl2N3OS | 59.73 59.92 | 3.87 4.11 | 9.50 9.73 |
| 65 | pentaF | A | chrom | 600 mg 21% |  | 463(M+) | CDCl3 4.04(d, J=5Hz, 1H), 5.82 (s, 1H), 6.94(s, 1H), 7.2-7.55(m, 1H) | C22H14F5N3OS |  |  |  |

| Ex. | R | R' | Method of Prep. | Solvent of Cryst.[a] | Yield, % | Mp, °C. | MS | 1HNMR | Formula | Analysis, % Theory/Found C | H | N |
|---|---|---|---|---|---|---|---|---|---|---|---|---|
| 66 | 2,3-dlCl | Me | A | EtOAc: hexane | 670 mg 76% | 172-4 | 439(M+) | DMSO 3.35(s, 3H), 3.88(s, 1H), 5.50 (s, 1H), 7.16-7.56(m, 13H), 9.26(s, 1H) | C23H19Cl2N3O2 | 62.74 62.55 | 4.35 4.26 | 9.54 9.37 |
| 67 | 4-CF3 | Me | A | chrom | 210 mg 40% |  | 439(M+) | CDCl3 3.36(s, 3H), 3.93(d, J=3Hz, 1H), 5.54(d, J=3Hz, 1H), 6.92(s, 1H), 7.15-7.6(m, 14H) | C24H20F3N3O2 | 65.60 65.35 | 4.59 4.51 | 9.56 9.30 |

TABLE I-continued

PHYSICAL CHEMISTRY DATA ON CCK/GASTRIN ANTAGONISTS

| Ex. | R | R' | Method of Prep. | Solvent of Cryst.[a] | Yield, % | Mp, °C. | MS | 1HNMR | Formula | Analysis, % Theory/Found C | H | N |
|---|---|---|---|---|---|---|---|---|---|---|---|---|
| 68 | 2,3-diCl | Ph | A | EtOAc | 170 mg 63% | 172-3 | 425(M+) | DMSO 2.5(m, 1H), 3.53(m, 1H), 5.72(s, 1H), 7.3-7.76(m, 11H), 7.95(s, 1H), 8.58 (s, 1H), 10.6(brs, 1H) | C22H17Cl2N3O2 | 61.96 52.20 | 4.02 4.04 | 9.86 9.94 |
| 69 | 4-Br | n-Bu | A | chrom | 670 mg 56% | | 415, 417 (M+'s for Br Isotopes) | DMSO 0.84(t, J=12Hz, 3H), 1.30(m, 2H), 1.46(m, 2H), 1.65(m, 2H), 3.29(s, 1H), 5.38(s, 1H), 7.2–7.6(m, 9H), 9.17 (s, 1H), 10.34(s, 1H) | C20H22BrN3O2 | | | |

TABLE I-continued
PHYSICAL CHEMISTRY DATA ON CCK/GASTRIN ANTAGONISTS

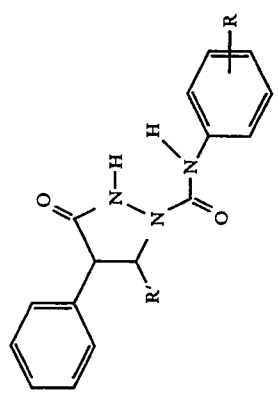

| Ex. | R | R' | Method of Prep. | Solvent of Cryst.[a] | Yield, % | Mp, °C. | MS | 1HNMR | Formula | Analysis, % Theory/Found C | H | N |
|---|---|---|---|---|---|---|---|---|---|---|---|---|
| 70 | 3-CF3 | n-Bu | A | chrom | 290 mg 21% | | 405(M+) | CDCl3 0.93(t, J=12Hz, 3H), 1.42(m, 2H), 1.5(m, 2H), 1.73(m, 1H), 1.83(m, 1H), 3.79(s, 1H), 4.83(m, 1H), 7.2-7.6 (m, 9H), 7.74(s, 1H), 7.83(s, 1H) | C21H22F3N3O2 | 62.21 62.40 | 5.47 5.66 | 10.36 10.26 |
| 71 | 4-CF3 | n-Bu | A | chrom | 136 mg 15% | 152-5 | 405(M+) | CDCl3 0.9(t, J=9Hz, 3H), 1.42(m, 2H), 1.51(m, 2H), 1.72(m, 1H), 1.88 (m, 1H), 3.53(s, 1H), 4.82(t, J=8Hz), 1H), 7.18-7.35(m, 5H), 7.44(ABq, J=8 Hz, Δν=18Hz, 4H), 7.65(s, 1H), 8.55(ν brs, 1H) | C21H22F3N3O2 | 62.21 61.97 | 5.47 5.56 | 10.36 10.22 |
| 72 | 4-Br | CH2Ph | A | EtOAc: hexane | 248 mg 51% | | 449, 451 (M+'s for Br Isotopes) | DMSO 2.97-3.15(m, 2H), 3.47(brs, 1H), 4.70(brs, 1H), 7.01(d, J=8Hz, 2H), 7.15-7.42(m, 12H), 9.05(brs, 1H), 10.47(brs, 1H) | C23H20BrN3O2 | 61.34 61.16 | 4.48 4.73 | 9.33 9.12 |
| 73 | 4-Br | i-Pr | A | chrom (EtOAc: hexane) | 45 mg 42% | | 401, 403 (M+'s for Br Isotopes) | CDCl3 1.12(d, J=6Hz, 6H), 2.05(m, J=7Hz, 1H), 3.64(s, 1H), 4.56(d, J=8 Hz, 1H), 7.20-7.51(m, 9H), 8.28(brs, 1H) | C19H20BrN3O2 | | | |

| Method | Solvent | Yield, | | | | | Analysis, % Theory/Found |

TABLE I-continued

PHYSICAL CHEMISTRY DATA ON CCK/GASTRIN ANTAGONISTS

| Ex. | R | X | Method of Prep. | Solvent of Cryst.[a] | Yield, % | Mp, °C. | MS | 1HNMR | Formula | C | H | N |
|---|---|---|---|---|---|---|---|---|---|---|---|---|
| 74 | 4-CF3 | — | E (Et3N) | c | 100 mg 6% | 72–5 | 410(M+) | CDCl3 3.89(d, J=4Hz, 1H), 5.16(brs, 1H), 7.18–7.26(m, 5H), 7.26–7.50(m, 8H), 7.50–7.57(m, 2H) | C23H17F3N2O2 | 67.31 67.57 | 4.18 4.45 | 6.83 6.64 |
| 75 | 3,4-dlCl | — | E (no base) | c | 508 mg 29% | 68–70 | 410, 412 (M+'s for Cl Isotopes) | CDCl3 3.89(d, J=4Hz, 1H), 5.18(brs, 1H), 7.14–7.48(m, 14H) | C22H16Cl2N2O2 | 64.25 54.21 | 3.92 3.99 | 6.81 6.60 |
| 76 | 3-CF3 | CH2 | E | chrom | 600 mg 17% | 66–68 | 424(M+) | CDCl3 3.47(s, 2H), 3.94(s, 1H), 5.30 (s, 1H), 7.0–7.8(m, 14H) | C24H19F3N2O2 | 67.92 57.76 | 4.51 4.56 | 6.60 6.79 |
| 77 | 4-CF3 | CH2 | E (no base) | c | 101 mg 6% | 66–68 | 424(M+) | CDCl3 3.48(brs, 2H), 3.91(d, J=4Hz, 1H), 5.28(brs, 1H), 7.04–7.5(m, 15H) | C24H19F3N2O2 | 67.92 67.78 | 4.51 4.56 | 6.60 6.45 |
| 78 | 3,4-dlCl | CH2 | E (Et3N) | Et2O: hexane | 1.0 g 17% | 70–72 | 426(M+) | CDCl3 3.36(brs, 2H), 3.93(d, J=Hz, 1H), 5.27(brs, 1H), 6.84(brs, 1H), 7.0 (brs, 1H), 7.08–7.5(m, 12H) | C23H19Cl2N2O2 | 64.95 64.93 | 4.27 4.67 | 6.58 6.60 |
| 79 | H | O | F | EtOAc: hexane | 980 mg 43% | 164–6 | 358(M+) | CDCl3 3.97(d, J=6Hz, 1H), 5.54(d, J=6Hz, 1H), 6.9–7.5(m, 16H) | C22H19N2O3 | 73.73 73.94 | 5.06 5.29 | 7.82 7.88 |
| 80 | 4-NO2 | O | F | EtOAc | 1.3 g 32% | 175–7 | 403(M+) | CDCl3 4.02(d, J=6Hz, 1H), 5.52(d, J=6Hz, 1H), 7.1–7.5(m, 12H), 8.19(d, J=15Hz, 2H), 9.25(brs, 1H) | C22H17N3O5 | 65.51 65.49 | 4.25 4.31 | 10.42 10.34 |
| 81 | 4-Br | S | B | EtOAc: hexane | 610 mg 13% | 156–7 | 452, 454 (M+'s for Br Isotopes) | CDCl3 3.97(d, J=4Hz, 1H), 5.58(d, J=4Hz, 1H), 7.25–7.55(m, 14H), 9.15 (brs, 1H) | C22H17BrN2O2S | 58.29 58.04 | 3.78 3.79 | 6.18 6.06 |

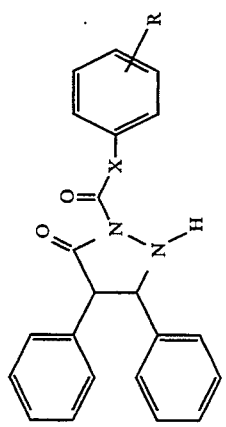

| Ex. | R | X | Method of Prep. | Solvent of Cryst.[a] | Yield, % | Mp, °C. | MS | 1HNMR | Formula | Analysis, % Theory/Found | | |
|---|---|---|---|---|---|---|---|---|---|---|---|---|
| | | | | | | | | | | C | H | N |
| 82 | 3-CF3 | NH | N | chrom (CH2Cl2) | 1.72 g 48% | | 425(M+) | CDCl3 4.22(d, J=12Hz, 1H), 4.82 (dd, J=9Hz, 12Hz, 1H), 5.46(d, J=9 Hz, 1H), 7.18–7.75(m, 13H), 7.84(s, 1H), 10.35(s, 1H) | C23H18F3N3O2 | | | |
| 83 | 4-CF3 | NH | N | chrom (CH2Cl2), then triturated with hexane | 530 mg 30% | 74–6 | 425(M+) | CDCl3 4.23(d, J=12Hz, 1H), 4.82 dd, J=9, 12Hz, 1H), 5.44(d, J=9Hz, 1H), 7.18–7.24(m, 2H), 7.3–7.42(m, 8H), 7.56–7.7(m, 4H), 10.4(brs, 1H) | C24H18F3N3O2 | 64.94 65.11 | 4.27 4.41 | 9.88 9.65 |

TABLE I-continued
PHYSICAL CHEMISTRY DATA ON CCK/GASTRIN ANTAGONISTS

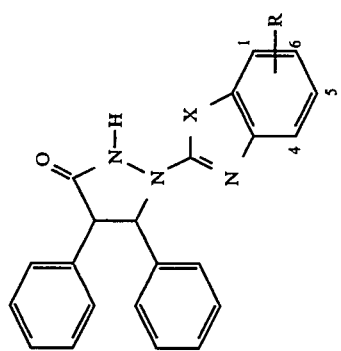

| Ex. | R | X | Method of Prep. | Solvent of Cryst.[a] | Yield, % | Mp, °C. | MS | 1HNMR | Formula | Analysis, % Theory/Found C | H | N |
|---|---|---|---|---|---|---|---|---|---|---|---|---|
| 84 | H | S | O (C6H6) | Et2O | 233 mg 42% | 186-8 | 371(M+) | CDCl3 4.05(d, 1H), 5.23(d, 1H), 7.15-7.68(m, 15H) | C22H17N3OS | 71.14 71.38 | 4.61 4.89 | 11.31 11.11 |
| 85 | 6-Br | S | O (PhMe) | Et2O: hexane | 1.67 g 57% | 180-6 | 449, 451 (M+'s for Br Isotopes) | CDCl3 4.06(d, J=7Hz, 1H), 5.24(d, J=7Hz, 1H), 7.16-7.52(m, 13H), 7.64 (d, J=1Hz, 1H) | C22H16BrN3OS | 58.67 58.87 | 3.58 3.83 | 9.33 9.08 |
| 86 | 4,5-dlCl | S | O (PhMe) | Et2O: hexane | 1.10 g 83% | 200-4 | 440(M+1 for Cl Isotopes) | CDCl3 4.13(d, J=8Hz, 1H), 5.19(d, J=8Hz, 1H), 7.18-7.45(m, 13H) | C22H14Cl2N3OS | 60.01 60.30 | 3.43 3.70 | 9.54 9.62 |
| 87 | H | O | O (PhMe) | Et2O | 660 mg 62% | 174-5.5 | 355(M+) | CDCl3 4.04(d, J=4.5Hz, 1H), 5.60(d, J=4.5Hz, 1H), 7.14-7.54(m, 15H) | C22H17N3O2 | 74.35 74.56 | 4.82 4.98 | 11.82 11.67 |

Structures for examples 88-108 below

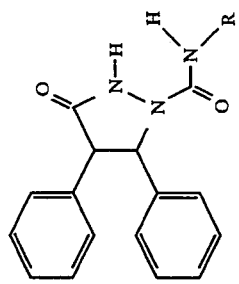

| Ex. | R | Method of Prep. | Solvent of Cryst.[a] | Yield, % | Mp, °C. | MS | 1HNMR | Formula | Analysis, % Theory/Found C | H | N |
|---|---|---|---|---|---|---|---|---|---|---|---|
| 88 | 3-Pyridyl | C | precipitated from reaction mixture | 3.5 g 73% | 208-10 | 358(M+) | DMSO 3.8(s, 1H), 5.54(s, 1H), 7.27-7.5(m, 11H), 7.94(m, 1H), 8.23(m, 1H), 8.7(m, 1H), 9.38(brs, 1H), 10.94(brs, 1H) | C21H18N4O2 | 70.38 70.34 | 5.06 5.16 | 15.63 15.35 |

TABLE I-continued

PHYSICAL CHEMISTRY DATA ON CCK/GASTRIN ANTAGONISTS

| | | | | | | | | | | | |
|---|---|---|---|---|---|---|---|---|---|---|---|
| 89 | 4-Pyridyl | C | chrom | 183 mg 28% | | 358(M+) | CDCl3 3.93(d, J=6Hz, 1H), 5.46(d, J=6Hz, 1H), 7.18-7.3(m, 10H), 7.62 (d, J=10Hz, 2H), 7.95(d, J=10Hz, 2H) | C21H18N4O2 | | | |
| 90 | 1-Naphthyl | A | EtOAc: hexane | 790 mg 33% | 145-7 | 407(M+) | CDCl3 4.03(d, J=6Hz, 1H), 5.51(d, J=6Hz, 1H), 6.8-7.8(m, 18H), 9.0(brs, 1H) | C26H21N3O2 | 76.64 76.41 | 5.19 4.33 | 10.31 10.12 |
| 91 | 2-Naphthyl | A | EtOAc: hexane | 1.13 g 44% | 172-4 | 407(M+) | CDCl3 4.02(d, J=6Hz, 1H), 5.60(d, J=6Hz, 1H), 7.1-7.9(m, 18H), 9.38 (brs, 1H) | C26H12N3O2 | 76.64 76.83 | 5.19 5.27 | 10.31 10.26 |
| 92 | 3-Quinolinyl | D | THF: PhMe (came out of reaction mixture) | 157 mg 12% | 244-6.5 | 409(M+) | DMSO 3.81(s, 1H), 5.57(d, 1H), 7.29-7.62(m, 12H), 7.85(d, J=8Hz, 1H), 7.91(d, J=8Hz, 1H), 8.44(d, J=2Hz, 1H), 8.97(d, J=2Hz, 1H), 9.62(brs, 1H), 11.00(brs, 1H) | C25H20N4O2 | 73.51 73.48 | 4.93 4.74 | 13.71 13.55 |
| 93 | 6-Quinolinyl | D | CH3CN: PhMe | 224 mg 32% | 222-5 | 408(M+) | DMSO 3.79(s, 1H), 5.58(s, 1H), 7.25-7.49(m, 11H), 7.85-7.93(m, 2H), 8.14(d, J=1.4Hz, 1H), 8.20(d, J=8Hz, 1H), 8.74(dd, J=1.4, 4.3Hz, 1H), 9.45(brs, 1H), 10.95(brs, 1H) | C25H20N4O2 | 73.51 73.68 | 4.94 5.09 | 13.72 13.57 |
| 94 | n-Bu | A | chrom | 2.68 g 76% | | 337 (M+) | DMSO 0.86(t, J=10Hz, 3H), 1.15(m, 2H), 1.38(m, 2H), 3.08(m, 2H), 3.62 (s, 1H), 5.47(s, 1H), 7.18(s, 1H), 7.3-7.46(m, 10H), 8.66(s, 1H) | C20H23N3O2 | 71.19 71.33 | 6.87 6.71 | 12.45 12.27 |
| 95 | c-Hexyl | A | EtOAc: hexane | 1.9 g 83% | 152-4 | 363(M+) | CDCl3 0.8-1.84(m, 10H), 3.6(m, 1H), 3.89(d, J=6Hz, 1H), 4.98(d, J=12Hz, 1H), 5.42(d, J=6Hz, 1H), 7.2-7.45(m, 10H), 8.66(s, 1H) | C22H25N3O2 | 72.70 72.59 | 6.93 7.03 | 11.56 11.30 |
| 96 | CH2Ph | A | chrom | 2.6 g 67% | | 371(M+) | CDCl3 3.86(d, J=6Hz, 1H), 4.31 (dABq, J=8Hz, Jab=20Hz, Δv=36Hz, 2H), 5.50(m, 1H), 5.51(d, J=6Hz, 1H), 7.07-7.43(m, 16H) | C23H21N3O2 | 74.37 74.11 | 5.70 5.77 | 11.31 11.12 |
| 97 | CH2Ph (N—Me) | M | chrom (EtOAc: hexane) | 380 mg 39% | | 385(M+) | CDCl3 2.65(s, 3H), 3.66(d, J=2Hz, 1H), 4.38(ABq, J=20Hz, Δv=72Hz, 2H), 4.94(d, J=2Hz, 1H), 6.9(m, 2H), 7.15-7.46(m, 13H), 7.9(brs, 1H) | C24H23N3O2 | | | |
| 98 | CH2Ph-2-Cl | M | chrom | 149 mg 15% | | 405(M+) | CDCl3 3.92(d, J=7Hz, 1H), 4.4(m, 2H), 5.39(d, J=7Hz, 1H), 5.55(t, J=6Hz, 1H), 7.15-7.43(m, 14H), 8.48(brs, 1H) | C23H20ClN3O2 | 68.06 68.30 | 4.97 5.13 | 10.35 10.01 |
| 99 | CH2Ph-3-Cl | C | EtOAc: hexane | 750 mg 29% | 133-6 | 405(M+) | CDCl3 3.88(d, J=6Hz, 1H), 4.26 (dABq, J=7Hz, Jab=17Hz, Δv=48Hz, 2H), 5.48(d, J=6Hz, 1H), 5.57(t, J=7Hz, 1H), 6.94-7.43(m, 14H), 8.9 | C23H20ClN3O2 | 68.03° 67.78 | 4.97 5.07 | 10.35 10.46 |
| 100 | CH2Ph-4-Cl | A | EtOAc: hexane | 182 mg 30% | 124-7 | 405(M+) | CDCl3 3.89(d, J=5Hz, 1H), 4.27 (dABq, J=6Hz, Jab=12Hz, Δv=42Hz, 2H), 5.48(t, J=6Hz, 1H), 5.50(d, J=5Hz, 1H), 6.98-7.44(m, 14H), 8.52 (brs, 1H) | C23H20ClN3O2 | 68.06 68.22 | 4.97 5.09 | 10.35 10.15 |
| 101 | CH(Me)Ph (S) | A | chrom | 900 mg | | 385(M+) | CDCl3⊖ 1.32(q, J=9Hz, 3H), 3.90 | C24H23N3O2 | 74.78 | 6.01 | 10.90 |

TABLE I-continued
PHYSICAL CHEMISTRY DATA ON CCK/GASTRIN ANTAGONISTS

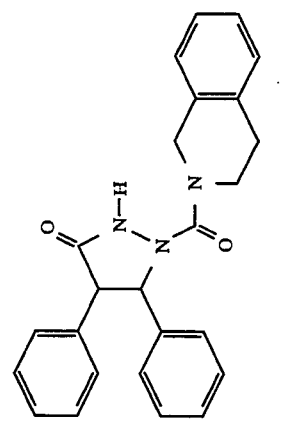

| | | Yield | Solvent | | | | Analysis, % Theory/Found | | |
|---|---|---|---|---|---|---|---|---|---|
| | (1:1 mixture of diastereomers - each optically active)[d] | 34% | | (dd, J=5Hz, 9Hz, 1H), 4.90(q, J=8Hz, 1H), 5.37(dd, J=9Hz, 36Hz, 1H), 5.45(t, J=5Hz, 1H), 7.0-7.44(m, 15H), 8.53(brs, 1H) | | | 75.04 | 6.10 | 10.94 |
| 102 | CH(Me)Ph (R) (1:1 mixture of diastereomers - each optically active)[f] | 172 mg 7% | chrom | 385(M+) | DMSO⊖ 1.20(t, J=6Hz, 3H), 3.60(s, ½H), 3.68(s, ½H), 4.83(m, 1H), 5.43(s, ½H), 5.52(s, ½H), 7.2-7.55(m, 15H), 10.56(s, 1H) | C24H23N3O2 | | | |
| 103 | CH(Me)Ph-4-Br (+/−) (single diastereomer obtained in crystallization)[g] | 670 mg 33% | EtOAc: hexane | 145-7 463, 465 (M+'s for Br Isotopes) | DMSO 1.41(d, J=8Hz, 3H), 3.62(s, 1H), 4.76(m, 1H), 5.42(s, 1H), 7.2-7.62(m, 15H), 10.56(s, 1H) | C24H22BrN3O2 | 62.08 62.27 | 4.78 4.75 | 9.05 8.95 |
| 104 | CH(Me)-1-Naphthyl (R) (c. 3:1 mixture of diastereomers - each optically active)[h] | 137 mg 12% | chrom | 435(M+) | CDCl3 (peaks for major isomer visible in plot) 1.5(d, J=9Hz, 3H), 3.86(d, J=6Hz, 1H), 5.48(d, J=6Hz, 1H), 5.74(m, 1H), 7.06–8.19(m, 19H) | C28H25N3O2 | | | |
| 105 | CH2CH2Ph | 720 mg 30% | chrom | 385(M+) | CDCl3 2.68(m, 2H), 3.42(m, 2H), 3.86(d, J=6Hz, 1H), 4.94(t, J=5Hz, 1H), 5.27(d, J=6Hz, 1H), 6.95-7.44 (m, 15H) | C24H23N3O2 | 74.78 74.49 | 6.01 6.15 | 10.90 10.74 |
| 106 | CH2CH2Ph-2-Cl | 2.2 g 63% | chrom | 419(M+) | CDCl3 2.82(m, 2H), 3.45(m, 2H), 3.85(d, J=7Hz, 1H), 5.02(t, J=6Hz, 1H), 5.25(d, J=7Hz, 1H), 5.95-7.4 (m, 14H), 8.58(brs, 1H) | C24H22ClN3O2 | 68.65 68.86 | 5.28 5.36 | 10.01 10.01 |
| 107 | CH2CH2Ph-4-Cl | 1.5 g 66% | chrom | 419(M+) | CDCl3 2.63(m, 2H), 3.40(m, 2H), 3.86(d, J=8Hz, 1H), 4.83(t, J=6Hz, 1H), 5.22(d, J=8Hz, 1H), 6.88-7.42 (m, 14H), 8.45(brs, 1H) | C24H22ClN3O2 | 68.65 68.84 | 5.28 5.36 | 10.01 7.96 |
| 108 | CH2CH2CH2Ph | 239 mg 48% | chrom (EtOAc: hexane) | 399(M+) | CDCl3 1.70(pentet, J=7Hz, 2H), 2.48 (t, J=7Hz, 2H), 3.18(m, 2H), 3.89(d, J=6Hz, 1H), 4.92(brt, J=6Hz, 1H), 5.35(d, J=6Hz, 1H), 7.02-7.46(m, 15H), 8.25(brs, 1H) | C25H25N3O2 | 75.16 74.89 | 6.31 6.26 | 10.52 10.27 |

Method

TABLE I-continued
PHYSICAL CHEMISTRY DATA ON CCK/GASTRIN ANTAGONISTS

| Example | of Prep. | of Cryst.a | % | Mp, °C. | MS | 1HNMR | Formula |
|---|---|---|---|---|---|---|---|
| 109 | B | chrom | 75 mg 4% | 160–6 | 397(M+) | CDCl3 2.58–2.82(m, 2H), 3.37–3.48(m, 1H), 3.54–3.62(m, 1H), 3.64(d, J=2, 1H), 4.37(d, J=3.5, 2H), 4.95(d, J=2,-1H), 6.78(m, 1H), 7.02–7.46(m, 13H), 8.18(brs, 1H) | C25H23N3O2 |

Structure for examples 110–133A below

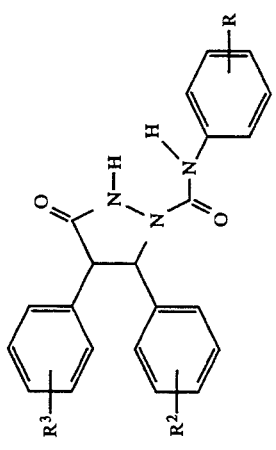

| Ex. | R1 | R2 | R3 | Meth. Prep. | Solvent of Cryst.a | Yield, % | Mp, °C. | MS | 1HNMR | Formula | Analysis, % Theory/Found C H N |
|---|---|---|---|---|---|---|---|---|---|---|---|
| 110 | 4-CF3 | 2-Cl | H | A | EtOAc | 185 mg 19% | | 459(M+) | DMSO 3.57(brs, 1H), 5.72(brs, 1H), 7.14–7.82(m, 13H), 9.72(brs, 1H), 11.01(brs, 1H) | C23H17BrClF3N3O2 | 60.07 3.73 9.14 / 59.85 3.80 8.82 |
| 111 | 4-CF3 | 3-CN | H | A | triturated with PhMe | 1.80 g 88% | | 450(M+) | DMSO 3.90(brs, 1H), 5.67(brs, 1H), 7.12–7.98(m, 13H), 9.63(brs, 1H), 10.83(brs, 1H) | C24H17F3N4O2 | 64.00 3.80 12.44 / 64.09 3.98 12.26 |
| 112 | 4-CF3 | 3-OMe | H | A | chrom (2× with EtOAc: hexane), then triturated with PheMe: hexane | 160 mg 9% | | 455(M+) | CDCl3 3.82(s, 3H), 4.03(d, J=7Hz, 1H), 5.51(d, J=7Hz, 1H), 6.92–7.00(m, 3H), 7.14–7.50(m, 10H), ~8.8(brs, 1H) | C24H20F3N3O3 | 63.29 4.43 9.23 / 63.00 4.36 9.03 |
| 113 | 4-CF3 | 4-N(Me)2 | H | A | EtOAc: hexane | 95 mg 32% | | 468(M+) | DMSO 2.90(s, 6H), 3.73(brs, 1H), 5.46(brs, 1H), 6.77(d, J=8Hz, 2H), 7.23–7.40(m, 7H), 7.62(d, J=8Hz, 2H), 7.76 (d, J=8Hz, 2H), 9.42(brs, 1H), 10.81(brs, 1H) | C25H23F3N4O2 | 64.10 4.95 11.96 / 64.25 5.18 11.71 |
| 114 | 4-Br | 2-Cl | H | A | PhMe, then EtOAc: hexane | 47 mg 10% | | 469, 471 (M+'s for Br Isotopes) | DMSO 3.53(brs, 1H), 5.72(brs, 1H), 7.12–7.60(m, 13H), 9.49(brs, 1H), 10.93(brs, 1H) | C22H17BrClN3O2 | 56.13 3.64 8.94 / 56.24 3.62 8.82 |
| 115 | 4-Br | 2-OMe | H | A | EtOAc: hexane | 52 mg 17% | | 465, 467 (M+'s for Br | CDCl3 3.72(s, 3H), 3.78(s, 3H), 5.50(brs, 1H), 6.87–7.04 (m, 3H), 7.27–7.52(m, 10H), | C23H20BrN3O3 | 59.24 4.32 9.01 / 59.45 4.23 8.90 |

TABLE I-continued

PHYSICAL CHEMISTRY DATA ON CCK/GASTRIN ANTAGONISTS

| # | R1 | R2 | | Recryst. | Yield | mp | MS | NMR | Formula | Analysis |
|---|----|----|---|----------|-------|-----|-----|-----|---------|----------|
| 116 | 4-Br (trans) | 2,3-diCl | A | triturated with Et2O, then CH2Cl2:hexane (to give CH2Cl2 hemi-solvate) | 1.89 g 69% | | Isotopes) 503, 505 (M+'s) 506, 508 (M+1's for Cl, Br Isotopes) | DMSO 3.58(s, 1H), 5.65(s, 1H), 5.70(s, 2Hfor ½ CH2Cl2), 7.28-7.46(m, 12H), 9.43(brs, 1H), 10.91(brs, 1H) 9.29(brs,1H) | C22H16BrCl2N3O2. ½CH2Cl2 | 49.35 3.13 7.67<br>49.60 3.25 7.78 |
| 117 | 4-Br (cis) | 2,3-diCl | A | CH2Cl2 (2×) | 76 mg 54% | 198-205 | 503, 505 507 (M+'s for Cl, Br Isotopes) | DMSO 5.04(d, J=10Hz, 1H), 6.30(m, 1H), 6.72(d, J=7Hz, 2H), 7.00-7.12(m, 3H), 7.30-7.60(m, 7H), 9.31(brs, 1H), 10.70(brs, 1H) | C22H16BrCl2N3O2 | 52.31 3.19 8.32<br>52.59 3.27 8.35 |
| 118 | 4-Br | 3-CONH2 | A | CH3CN | 237 mg 45% | 210-3 | 479, 481 (M+1's for Br Isotopes) | DMSO 3.78(s, 1H), 5.55(s, 1H), 7.25-7.59(m, 12H), 7.80 (d, J=8Hz, 1H), 7.94(d, J=24Hz, 2H), 9.28(s, 1H), 10.78(brs, 1H) | C23H19BrN4O3 | 57.63 4.00 11.69<br>57.57 3.96 11.66 |
| 119 | 4-Br | 4-NO2 | A | EtOAc: PhMe | 343 mg 60% | | 480, 482(M+'s for Br Isotopes) | DMSO 3.88(brs, 1H), 5.69(brs, 1H), 7.30-7.53(m, 9H), 7.76 (brd, J=7Hz, 2H), 8.31(d, J=8Hz, 2H), 9.39(brs, 1H), 10.93 (brs, 1H) | C22H17BrN4O4 | 54.90 3.56 11.64<br>55.15 3.64 11.55 |
| 120 | 3-CF3, 4-Cl | 2-Cl | A | EtOAc: hexane | 604 mg 44% | | 493, 495(M+'s for Br Isotopes) | DMSO 3.58(brs, 1H), 5.72(brs, 1H), 7.30-7.50(m, 7H), 7.58-7.67(m, 3H), 7.93(d, J=9Hz, 1H), 8.15(brs, 1H), 9.83 (brs, 1H), 11.04(brs, 1H) | C23H16Cl2F3N3O2 | 55.89 3.26 8.50<br>55.85 3.21 8.43 |
| 121 | 4-i-Pr | 2-Cl | A | EtOAc: hexane | 514 mg 43% | | 434(M+1) | DMSO 1.18(d, J=7Hz, 6H), 2.84(m, J=7Hz, 1H), 3.51(brs, 1H), 5.74(m, 1H), 7.14-7.64(m, 13H), 9.27(brs, 1H), 10.88(brs, 1H) | C25H24ClN3O2 | 69.20 5.58 9.68<br>69.00 5.55 9.73 |
| 122 | 4-Br | H | A | EtOAc | 750 mg 43% | 182-2.5 | 470(M+1) | DMSO 4.16(brs, 1H), 5.66(brs, 1H), 7.48-7.88(m, 13H), 9.56(brs, 1H), 11.26(brs, 1H) | C22H17BrClN3O2 | 56.13 3.64 8.93<br>56.35 3.62 8.92 |
| 123 | 4-Br | H. | A | EtOAc: hexane | 520 mg 30% | 154-5 | 467(M+) | CDCl3 3.72(s, 3H), 4.94(d, J=6Hz, 1H), 5.57(d, J=6Hz, 1H), 6.74-6.88(m, 3H), 7.04-7.32(m, 7H), 7.42(brs, 4H), 9.2(brs, 1H) | C23H20BrN3O3 | 59.24 4.32 9.01<br>59.44 4.39 9.06 |
| 124 | 4-Br | H | A | Et2O: hexane | 2.24 g 91% | 148-51 | 493, 495 (M+'s for Br Isotopes) | CDCl3 1.22(t, J=6Hz, 6H), 3.90(d, J=4.5Hz, 1H), 4.43 (septet, J=6Hz, 1H), 5.58(d, J=4.5Hz, 1H), 6.74-6.82(m, 3H), 7.08(dd, J=2.9Hz, 2H), 7.19-7.29(m, 5H), 7.36-7.42 (m, 5H) | C25H24BrN3O3 | 60.74 4.89 8.50<br>60.53 4.94 8.70 |
| 125 | 4-Br | H | A | CH2Cl2: | 1.32 g | 150-1.5 | 480, 482 | DMSO 4.05(s, 1H), 5.61(s, | C22H17BrN4O4 | 54.90 3.56 11.64 |

TABLE I-continued
PHYSICAL CHEMISTRY DATA ON CCK/GASTRIN ANTAGONISTS

| # | Sub1 | Sub2 | Sub3 | Method | Solvent | Yield | mp | MS (M+'s for Br Isotopes) | NMR | Formula | C calc/found | H calc/found | N calc/found |
|---|------|------|------|--------|---------|-------|-----|-----|-----|---------|------|------|------|
| | | | | | hexane | 48% | | | 1H), 7.27-7.52(m, 9H), 7.66(t, J=8Hz, 1H), 7.82(d, J=8Hz, 1H), 8.16(d, J=8, 1H), 8.22(s, 1H), 9.34(brs, 1H), 10.95(brs, 1H) | | 54.63 | 3.67 | 11.74 |
| 126 | 4-Br | H | 3-Cl | A | EtOAc: hexane | 232 mg 27% | 142-3 | 470(M+1) | CDCl3 4.0(d, J=6Hz, 1H), 5.46(d, J=6Hz, 1H), 6.87(brs, 1H), 7.0-7.12(m, 3H), 7.22-7.54(m, 10H), 8.78(brs, 1H) | C22H17BrClN3O2 | 56.13 56.21 | 3.64 3.76 | 8.93 8.84 |
| 127 | 4-Br | H | 3-Br | A | chrom, then triturated with Et2O: hexane | 128 mg 17% | | 515, 517 (M+'s), 516(M+1 for Br Isotopes) | CDCl3 3.94(brd, J=4Hz, 1H), 5.46(brd, J=4Hz, 1H), 7.04-7.44(m, 15H) | C22H17Br2N3O2 | 51.29 51.66 | 3.33 3.60 | 8.16 7.88 |
| 128 | 4-Br | H | 4-OMe | A | chrom (EtOAc), then triturated with hexane | 296 mg 34% | | 467(M+) | CDCl3 3.78(s, 3H), 3.95(d, J=6Hz, 1H), 5.49(d, J=6Hz, 1H), 6.85(d, J=12Hz, 2H), 7.0-7.18(m, 5H), 7.24-7.5(m, 7H), 9.1(brs, 1H) | C23H20BrN3O3 | 59.24 59.30 | 4.32 4.53 | 9.01 8.78 |
| 129 | 4-Br | H | 4-Cl | A | triturated with Et2O | 1.92 g 82% | 1.72-4.5 | 469, 471 473 (M+'s), 470(M+1 for Cl Br Isotopes) | DMSO 3.78(s, 1H), 5.49(s, 1H), 7.28-7.50(m, 13H), 9.22 (brs, 1H), 10.84(brs, 1H) | C22H17BrClN3O2 | 56.13 56.03 | 3.64 3.57 | 8.93 9.0 |
| 130 | 4-CF3 | H | 2-Cl | A | triturated with EtOAc: hexane | 260 mg 38% | 178-9 | 459(M+) | CDCl3 4.4(d, J=6Hz, 1H), 5.58(d, J=6Hz, 1H), 7.2-7.54 (m, 13H), 7.64(brs, 1H), 9.48 (brs, 1H) | C23H17ClF3N3O2 | 60.07 60.07 | 3.73 3.77 | 9.14 9.18 |
| 131 | 3-CF3, 4-Cl | H | 2-Cl | A | triturated with EtOAc: hexane | 250 mg 34% | 109-10 | 493(M+) | CDCl3 4.38(d, J=6Hz, 1H), 5.6(d, J=6Hz, 1H), 7.16-7.66 (m, 12H), 7.86(brs, 1H), 9.58 (brs, 1H) | C23H16Cl2F3N3O2 | 55.89 55.60 | 3.26 3.24 | 8.50 8.45 |
| 132 | 4-i-Pr | H | 2-Cl | A | EtOAc: hexane | 200 mg 31% | 226-7 | 433(M+) | DMSO 1.16(d, J=7Hz, 6H), 2.82(m, 1H), 3.92(brs, 1H), 5.46(brs, 1H), 7.12(d, J=12Hz, 2H), 7.28-7.64(m, 11H), 9.14(brs, 1H), 10.98(brs, 1H) | C25H24ClN3O2 | 69.20 69.45 | 5.57 5.60 | 9.68 9.58 |
| 133 | 4-Br (trans) | 2-Cl | | A | EtOAc: hexane | 4.32 g. 88% | | 505(M+) | DMSO 4.02(brs, 1H), 5.75(brs, 1H), 7.28-7.58(m, 12H), 9.41(brs, 1H), 11.06(brs, 1H) | C22H16BrCl2N3O2 | 52.30 52.07 | 3.19 3.27 | 8.32 8.09 |
| 133A | 4-Br (cis) | 2-Cl | | A (THF) | EtAOc: hexane | 113 mg 48% | | 505(M+) | DMSO 5.26(d, J=8Hz, 1H), 6.20(brs, 1H), 6.36(d, J=9Hz, 1H), 6.85(t, J=9Hz, 1H), 7.06-7.70(m, 10H), 9.34(brs, 1H), 10.74(brs, 1H) | C22H16BrCl2N3O2 | 52.31 52.23 | 3.19 3.32 | 8.32 8.47 |

TABLE I-continued
PHYSICAL CHEMISTRY DATA ON CCK/GASTRIN ANTAGONISTS

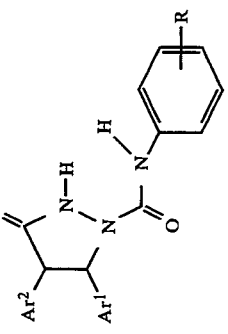

| Ex. | R1 | Ar1 | Ar2 | Meth. Prep. | Solvent of Cryst.[a] | Yield, % | Mp, °C. | MS | 1HNMR | Formula | Analysis, % Theory/Found | | |
|---|---|---|---|---|---|---|---|---|---|---|---|---|---|
| | | | | | | | | | | | C | H | N |
| 134 | 4-Br | Ph | 1-Naphthyl | A | Et2O:hexane | 1.48 g 61% | 187-9 | 486, 488 (M+1's for Br Isotopes) | CDCl3 4.70(d, J=6Hz, 1H), 5.59 (d, J=6Hz, 1H), 6.97(d, J=9Hz, 2H), 7.15-7.52(m, 12H), 7.70-7.88(m, 3H), 9.10(brs, 1H) | C26H20BrN3O2 | 64.21 64.02 | 4.15 4.20 | 8.64 8.61 |
| 135 | 4-Br | 3-Pyridyl | Ph | A | EtOAc (2X, then chrom, then EtOAc | 848 mg 24% | 184-87.5 | 437, 439 (M+1's for Br Isotopes) | DMSO 3.84(s, 1H), 5.56(s, 1H), 7.23-7.46(m, 10H), 7.83(d, J=8Hz 1H), 8.53(dd, J=1.1, 4.5Hz, 1H), 8.65(d, J=1.7 Hz, 1H), 9.28 (s, 1H), 10.86(brs, 1H) | C21H17BrN4O2 | 57.66 57.74 | 3.92 3.99 | 12.81 13.07 |

[a]Includes other methods of purification such as chromatography (chrom), trituration, and precipitation, as indicated. If only solvents are given, compound was purified by recrystallization from those solvents. For other methods of purification, solvents used follow in parentheses.
[b]After recrystallization from EtOAc:hexane.
[c]Purified by extraction into 1N NaOH, followed by acidification with 1N HCl and extraction into organic solvent (Et2O or EtOAc). Evaporation of solvent gave material homogeneous by TLC and of satisfactory purity.
[d]Prepared using (S)-(−)-α-methylbenzylisocyanate
[e]All splitting patterns reported are those apparent upon visual inspection of plot, and reflect a combination of true proton-proton magnetic couplings, and multiplicity due to presence of a mixture of two diasteromers.
[f]Prepared using R-(+)-α-methylbenzylisocyanate
[g]Prepared using (±)-4-bromo-α-methylbenzylisocyanate.
[h]Prepared using (R)-(−)-1-(1-naphthyl)ethylisocyanate

EXAMPLE 136

1-[(2-Naphthyl)aminothiocarbonyl]-4,5-diphenyl-3-pyrazolidinone [Method G]

2-Aminonaphthalene (2.95 g, 20.6 mmol) was dissolved in 230 mL CHCl₃ under nitrogen. Triethytamlne (11.5 mL. 8.35 g, 82.5 retool, 4.00 eq) was added and the mixture was cooled in an ice bath. Thiophosgene (3.30 mL. 43.3 mmol, 2.0 eq), dissolved in 90 mL CHCl₃. was added slowly over 1 hr. Stirring was continued for 2 hr at room temperature, then the mixture was partitioned between $H_2O$ and $CHCl_3$. The organic phase was separated, washed with $H_2O$ and two times with 1.0 N HCl, then dripped through $Na_2SO_4$ to remove water and evaporated in vacuo to yield 4.29 g (>100%) of a brown oil which solidified. NMR indicated the desired 2-naphthylisothiocyanate and contaminants: ¹H NMR (CDCl₃) 7.30–7.85 (m, 7H).

4,5-Diphenyl-3-pyrazolidinone (1.00 g, 4.20 mmol) was dissolved in 10 mL THF under retrogan and a solution of crude 2-naphthylisothiocyanate (obtained above: 0.93 g, c. 5.0 mmol, c. 1.2 eq) in 10 mL THF was added. After stirring overnight, TLC indicated the presence of unreacted pyrazolidinone, so more 2-naphthylisothiocyanate (0.39 g, c. 0.50 eq) was added in THF. After stirring an additional 1 hr, TLC still indicated some pyrazolidinone. After removal of solvent in vacuo, the residue was partially purified on two sequential silica columns (EtOAc:hexane with 0.5% HOAc). The material so obtained was dissolved in CHCl₃ and extracted three times with pH 10 buffer. The combined aqueous extracts were acidified with 1.0N HCl and then extracted three times with Et₂O. The organic extracts were combined, dripped through $Na_2SO_4$ to remove water, and evaporated in vacuo to obtain 0.60 g of material, which TLC indicated still contained impurities. The entire extractive procedure was then repeated (using CH₂Cl₂ as the organic phase throughout), to afford 311 mg (17%) of a pate yellow foam:

¹H NMR (CDCl₃) δ 4.11 (d, J=5 Hz, 1H), 5.73 (d, J=5 Hz, 1H), 7.26–7.56 (m, 13H), 7.67–7.82 (m, 4H); MS 423 (M+); titration $pK_a$ 5.8.

Analysis for $C_{26}H_{21}N_3OS$: calculated C 73.73, H 5.00, N 9.92; found C 73.75, H 5.13, N 9.97.

TABLE II

PHYSICAL CHEMISTRY DATA ON CCK/GASTRIN ANTAGONISTS

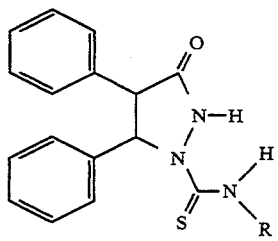

| Ex. | R | Method of Prep. | Solvent of Cryst.[a] | Yield, % | Mp. °C. | MS | 1HNMR | Formula | Analysis, % Theory/Found C | H | N |
|---|---|---|---|---|---|---|---|---|---|---|---|
| 137 | 3-Quinolinyl | G | triturated with PhMe | 1.23 g 69% | | 424, 425 (M+, M+1) | DMSO 3.99(s, 1H), 6.18(br s, 1H), 7.12–7.52(m, 10H), 7.51 (td, J=15, 2Hz, 1H), 7.60(td, J=15, 2Hz, 1H), 7.98(t, J=15Hz, 2H), 8.44(s, 1H), 8.98 (d, J=3Hz, 1H), 10.22 (br s, 1H), 11.96(br s, 1H) | C25H20N4OS | 70.73 70.52 | 4.75 4.86 | 13.20 12.98 |
| 138 | CH2Ph-3,4-diCl | G | chrom (EtOAc hexane + HOAc) | 1.38 g 69% | | 456, 458 (M+'s for Br Isotopes) | CDCl3 4.00(d, J=5Hz, 1H), 4.48 (dd, J=5, 17Hz, 1H), 4.76(dd, J=7, 17Hz, 1H), 5.65(d, J=5Hz, 1H), 6.05(br s, 1H), 6.87(dd, J=2.9Hz, 1H), 7.07–7.46(m, 12H), 9.45(br s, 1H) | C23H19Cl2N3OS | 60.53 60.30 | 4.20 4.33 | 9.21 8.95 |

[a]Includes other methods of purification such as chromatography (chrom), trituration, and precipitation, as indicated. If only solvents are given, compound was purified by recrystallization from those solvents. For other methods of purification, solvents used follow in parentheses.

PREPARATION 1

(R)-α-Methylbenzylphenylcarbonate (R)-α-Methylbenzyl alcohol (4.34 g, 35.5 mmol) was dissolved in 120 mL CH₂Cl₂ under nitrogen and pyridine (4.31 mL, 1.5 eq) was added. The mixture was cooled in an ice bath and a solution of phenyl chloroformate in 30 mL CH₂Cl₂ slowly added. After addition, the ice bath was removed and stirring continued overnight at room temperature. The mixture was partitioned between CH₂Cl₂ and 1.0N HCl, then the organic layer separated, dripped through Na₂SO₄ to remove water, and the solvent evaporated in vacuo to obtain 8.34 g of an oil, which was used without further purification (97% crude yield):

¹H NMR (CDCl₃) δ 1.69 (d, J=7 Hz, 3H), 5.83 (q, J=7 Hz, 1H), 7.14–7.46 (m, 10H); MS 242 (M+); $[\alpha]_D = +119.6°$, $[\alpha]_{365} = +428.8°$ (c=1.02. MeOH).

Analysis for $C_{15}H_{14}O_3$: calculated C 74.36, H 5.82: found C 74.06, H 5.98.

EXAMPLE 139A/139B

Diastereomers A and B of 1-[((R)-α-Methylbenzyl)oxycarbonyl]-trans-4,5-diphenyl-3-pyrazolidinone (+)-trans-4,5-Diphenyl-3-pyrazolidinone (8.13 g, 34.2 mmol) was dissolved in 150 mL THF under nitrogen, cooled in an ice bath, and 1.43 g NaH (60% in mineral oil; hydride content 0.86 g, 35.7 mmol, 1.05 eq) was added. The mixture was stirred for 15 min at ice bath temperature and 30 min at room temperature. A solution of (R)-α-methylbenzylphenylcarbonate [from Preparation 1] (8.25 g, 34.1 mmol, 1.00 eq) in THF was then added over 10 min and the mixture stirred a further 40 min. After partitioning between $Et_2O$ and 1.0N HCl, the organic phase was separated, and the aqueous phase extracted a second time with $Et_2O$. The organic extracts were combined, dripped through $Na_2SO_4$ to remove water, and evaporated to provide 17.45 g of a crude mixture of the title products. Preliminary purification (without separation of diastereomers) was achieved on two sequential silica columns (EtOAc:hexane). Final purification and separation of diastereomers A and B was accomplished via HPLC (Waters RCM 1.2.3 system; 3 piggybacked Nova C18 columns, each 40×100 mm, 6 μM particles; flow rate=45 mL/min (c. 1100 psi); UV detection at 245 nm/1.0 AUFS; eluent 64% MeOH:$H_2O$ with 2.5% HOAc; loading c. 50–60 mg/injection). Three fractions were collected: the first was highly enriched in diastereomer A, the second contained a mixture of A and B (which was recycled), and the third was highly enriched in diastereomer B. The first fractions from various runs were combined, evaporated, and the residue lyophilized to yield diastereomer A.

Processing of the third fractions from various runs in a similar fashion yielded diastereomer B. The diastereomeric purity of A and B were determined on analytical HPLC (Nova C18 column: eluent 70% MeOH:$H_2O$ with 1% HOAc at 1500 psi: UV detection at 254 nm), anti were typically in the range 95–100%.

Diastereomer A:

$^1$H NMR (CDCl$_3$) δ 1.48 (d, J=8 Hz. 3H), 3.88 (d, J=6 Hz, 1H), 5.34(d, J-6 Hz. 1H), 5.81 (q, J=8 Hz. 1H), 7.03 (m, 1H), 7.15–7.42 (m, 14H), 8.08 (br s, 1H); MS 386 (M+); titration p$K_a$ 8.7: [α]$_D$=−23.1°, [α]$_{365}$=−71.0° (c=0.99, MeOH).

Analysis for $C_{24}H_{22}N_2O_3$: calculated C 74.59, H 5.74, N 7.25; fount C 74.52, H 5.97, N 7.24.

Diastereomer B:

$^1$H NMR (CDCl$_3$) δ 1.42 (d, J=7 Hz, 3H), 3.88 (d, J=5 Hz, 1H), 5.34 (s, 1H), 5.80 (q, J=7 Hz, 1H), 7.14–7.43 (m, 15H), 8.30 (br s, 1H); MS 386 (M+); titration p$K_a$ 8.6: [α]$_D$=−18.7°, [α]$_{365}$=−122.2° (c=1.01. MeOH).

Analysis for $C_{24}H_{22}N_2O_3$: calculated C 74.59, H 5.74, N 7.25: found C 74.79. H 5.84, N 7.22.

PREPARATION 2

(+)-trans-4,5-Diphenyl-3-pyrazolidinone

A thick-walled glass hydrogenation tube was charged with diastereomer B of 1-[((R)-α-methylbenzyl)oxycarbonyl]-trans-4,5-diphenyl-3-pyrazolidinone [from Example 139A/139B] (226 mg, 0.586 mmol), 15.0 mL THF and 5% Pd/C catalyst (112 mg) and was shaken on a Parr apparatus under an atmosphere of hydrogen at c. 50 psi pressure for 15.5 hr. The catalyst was filtered off using Celite and washed with THF. The filtrate was evaporated in vacuo to obtain 134 mg (96%) of a white foam:

$^1$H NMR (CDCl$_3$) δ 3.99 (d, J=11 Hz, 1H), 4.66 (br s, 1H), 4.74 (d, J=11 Hz. 1H), 7.20–7.39 (m, 10H), 8.63 (br s, 1H).

PREPARATION 3

(-)-trans-4,5-Diphenyl-3-pyrazolidinone

Diastereomer A of 1-[((R)-α-methylbenzyl)oxycarbonyl]-trans-4,5-diphenyl-3-pyrazolidinone [from Example 139A/139B] (261 mg, 0.677 mmol) was subjected to hydrogenolysis (17 mL THF, 128 mg 5% Pd/C) and workup as described in Preparation 2 to obtain 154 mg (96%) of a white foam:

$^1$H NMR (CDCl$_3$) δ 4.01 (d, J=11 Hz, 1H), 4.38 (br s, 1H), 5.81 (br s, 1H), 7.18–7.41 (m, 10H); [α]$_D$=−76°, [α]$_{365}$=−278° (c=1.08, CHCl$_3$).

EXAMPLE 140

(-)-trans-1-[(4-Bromophenyl)aminocarbonyl]-4,5-diphenyl-3-pyrazolidinone (+)-trans-4,5-Diphenyl-3-pyrazolidinone [from Preparation 2] (70.7 mg, 0.297 mmol) was dissolved in 1.0 mL THF under an argon atmosphere and treated with a solution of 4-bromophenylisocyanate (67.9 mg, 0.343 mmol, 1.15 eq) in 1.0 mL THF. The mixture was stirred for 45 min, then time solvents removed in vacuo. The product was initially purified by chromatography (EtOAc:toluene) to provide 90.4 mg of material, in which impurities were still apparent by NMR. This was dissolved in toluene and hexane added until a precipitate appeared. Solvents were carefully removed by pipette and the remaining solid dried on a vacuum pump, giving 77.3 mg (60%) of a white solid:

$^1$H NMR (CDCl$_3$) δ 4.01 (d, J=7 Hz, 1 H), 5.52 (d, J=7 Hz, 1H), 6.90–7.50 (m, 15H), 8.60 (br s, 1 H); MS 435, 437 (M+'s for Br isotopes); [α]$_D$=−39°, [α]$_{365}$=−293° (c=1.26, CHCl$_3$).

Analysis for $C_{22}H_{18}BrN_3O_2$: calculated C 60.56, H 4.16, N 9.63: found C 61.43, H 4.29, N 9.58. Enantiomeric excess (ee) 95.1%. based on HPLC assay of diastereomeric purity of precursor diastereomer B from Example 139A/139B.

EXAMPLE 141

(+)-trans-1-[(4-Bromophenyl)aminocarbonyl]-4,5-diphenyl-3pyrazolidinone (−)-trans-4,5-Diphenyl-3-pyrazolidinone {from Preparation 3] (82.9 mg, 0.348 mmol) was dissolved in 1.0 mL THF under an argon atmosphere and treated with a solution of 4-bromophenylisocyanate (76.8 mg, 0.388 mmol, 1.11 eq) in 1.0 mL THF. The mixture was stirred for 30 min, then the solvents removed in vacuo. The product was initially purified by chromatography (33→66% EtOAc:toluene gradient) to provide 51.6 mg of material, in which impurities were still apparent by NMR. This was triturated with hexane, then the resulting solid recrystallized from $CH_2Cl_2$:toluene: hexane. Careful removal of solvents via pipette and drying on a vacuum pump yielded 20.8 mg (14%) of a white solid:

$^1$H NMR (CDCl$_3$) δ 4.02 (d, J=7 Hz, 1H), 5.52 (d, J=7 Hz, 1H), 6.90–7.50 (m, 15H), 8.60 (br s, 1H); MS 435, 437 (M+'s for Br isotopes); [α]$_D$=+40°, [α]$_{365}$=+299° (c=0.88, CHCl$_3$).

Analysis for $C_{22}H_{18}BrN_3O_2$: calculated C 60.56, H 4.16, N 9.63: found C 61.93, H 4.43, N 9.37. Enantiomeric excess (ee) 100%, based on HPLC assay of diastereomeric purity of precursor diastereomer A from Example 139A/139B.

EXAMPLE 142

(+)-trans-1-[(4-Chloro-3-trifluoromethylphenyl)-aminothiocarbonyl]-4,5-diphenyl-3-pyrazolidinone (+)-trans-4,5-Diphenyl-3-pyrazolidinone [from Preparation 2] (134 mg, 0.561 mmol) was dissolved in 8.0 mL THF under nitrogen and a solution of 4-chloro-3-trifluoromethylphenylisothiocyanate (137 mg, 0.578 mmol, 1.03 eq) in 2 mL THF was added. The mixture was stirred for 12 hr and then the solvent removed in vacuo. The residue was first purified on two sequential silica columns (EtOAc:hexane with 0.5% HOAc). The partially purified material so obtained (155 mg) was dissolved in $CH_2Cl_2$ and extracted three times with pH 10 buffer. The aqueous extracts were combined, acidified with 1.0N HCl, and extracted three times with $CH_2Cl_2$. The organic extracts were combined, dripped through $Na_2SO_4$ to remove water, and evaporated in vacuo to give 93.5 mg (35%) of the product as a pale yellow foam:

$^1H$ NMR ($CDCl_3$) δ 4.10 (d, J=5 Hz, 1H), 5.74 (d, J=5 Hz, 1H), 7.35–7.60 (m, 15H); MS 475 (M+) ; $[\alpha]_D = +32°$, $[\alpha]_{365} = -116°$ (c=1.06, $CHCl_3$).

Analysis for $C_{23}H_{17}ClF_3N_3OS$: calculated C 58.05, H 3.60, N 8.83; found C 57.86, H 3.79, N 8.69. Enantiomeric excess (ee) 98.6%, based on HPLC assay of diastereomeric purity of precursor diastereomer B from Example 139A/139B.

EXAMPLE 143

(−)-trans-1-[(4-Chloro-3-trifluoromethylphenyl)-aminothiocarbonyl]-4,5-diphenyl-3-pyrazolidinone (−)-trans-4,5-Diphenyl-3-pyrazolidinone [from Preparation 3] (147 mg, 0.617 mmol) was dissolved in 8.0 mL THF under nitrogen and treated with a solution of 4-chloro-3-trifluoromethylphenylisothiocyanate (160 mg, 0.673 mmol, 1.09 eq) in 3 mL THF. The mixture was stirred for 1.5 hr and the solvent then removed in vacuo. The product was purified as for Example 142, except that the initial chromatographic steps were omitted, and the entire extractive procedure was repeated a second time, to yield 145 mg (49%) of a pale yellow foam:

$^1H$ NMR ($CDCl_3$) δ 4.14 (d, J=5 Hz, 1H), 5.74 (d, J=5 Hz, 1H), 7.35–7.60 (m, 15H); MS 475 (M+); $[\alpha]_D = -28°$, $[\alpha]_{365} = +128°$ (c=1.15, $CHCl_3$).

Analysis for $C_{23}H_{17}ClF_3N_3OS$: calculated C 58.05, H 3.60, N 8.83; found C 57.77, H 3.67, N 8.64. Enantiomeric excess (ee) 97.2%, based on HPLC assay of diastereomeric purity of precursor diastereomer A from Example 139A/139B.

TEST PROCEDURES FOR CCK AND GASTRIN RECEPTOR BINDING (IC$_{50}$)

Brain

Brain CCK receptor binding was performed using mouse brain membranes according to the method of Chang and Lotti (*Proc. Natl. Acad. Sci.* 83: 4923–4926, 1986). Male CF-1 mice, 23–25 g were sacrificed by cervical dislocation, the forebrain removed and placed in ice cold 50 mM Tris buffer, pH 7.4. The tissue was homogenized in 100 volumes of the Tris buffer with a Brinkman Polytron or Tekmar Tissumizer and then centrifuged at 40,000 g for 10 min. Pellets were resuspended in Tris buffer, centrifuged as above and then resuspended in 100 volumes of assay buffer, pH 6.5 (20 mM N-2-hydroxyethyl-piperazine-N'-2-ethane sulfonic acid (HEPES), 1 mM ethylene glycol his (2-aminoethyl ether-N,N,N',N'-tetraacetic acid) (EGTA), 5 mM $MgCl_2$, 130 mM NaCl, and 0.25 mg/ml bacitracin). The binding assay consisted of 50 μL of compound (or buffer for total binding), 50 μL of $^{125}I$-CCK-8 sulfate (20 pM) (Amersham IM-159), 200 μL of assay buffer and 200 μL of homogenate (80–120 μg protein). The samples were incubated at room temperature (25°) for 2 hours, and they were then filtered through GF/B glass fiber filters (soaked in wash buffer for 2 hours before use) using a 48 well Brandel cell harvester designed for receptor binding. The filters were washed twice with 3 ml of 50 mM Tris buffer, pH 7.4, containing 0.01% BSA and then counted for radioactivity in plastic tubes with a Micromedic 10/600 automatic gamma counter.

Compounds were dissolved in dimethyl sulfoxide (DMSO) at a concentration of 10 mM and then further diluted with assay buffer. The concentration of DMSO in the incubation was 0.1% or less and had no effect on the assay at that level. IC-50 values of displacement curves were determined using 7 concentrations of compound and were calculated using the ALLFIT computer program of DeLean, Munson and Rodbard (*Am. J. Physiol.* 235: E97-E102, 1978). Non-specific binding was determined as the displacement of the radioligand by 100 nM CCK-8 sulfate.

Pancreas

Binding to peripheral type CCK receptors in rat pancreas was done according to the method of Chang et al. (*Mol. Pharmacol.* 30: 212–217, 1986) using $^3H$-L364,718. Pancreas was obtained from male Sprague-Dawley rats, 150–200 g, after decapitation, and dissected free from adipose and connective tissue. The tissue was homogenized in 30 volumes of 50 mM Tris buffer, pH 7.4 and centrifuged at 40,000 g for 10 min. The tissue pellet was washed by resuspension and centrifugation as described above. The final pellet was suspended in 500 volumes of assay buffer (50 mM Tris buffer, pH 7.4, 5 mM $MgCl_2$, 0.14 mg/ml bacitracin, and 5 mM dithiothreitol) to give a protein concentration of 30–60 μg/200 μl. Reagent volumes for the assay were the same as those used for CCK binding to brain membranes. Tritium labeled L-364,718 (Dupont NEN, NET-971) was used as the ligand at a concentration of 0.4–0.6 nM. The samples were incubated 1 hour at room temperature and then filtered as described for the CCK-brain receptor. Scintillation cocktail was added to the filters which were counted for radioactivity using a Micromedic Taurus automatic liquid scintillation counter.

Compound samples were prepared and IC-50 values were determined as described for the CCK-brain experiments. Non-specific binding was that amount left bound to the filters after adding 100 nM L-364,718.

Gastric Mucosa

The method used for gastrin binding to guinea pig stomach mucosal membranes was similar to that described by Takeuchi, Speir and Johnson (*Am. J. Physiol.* 237(3): E284-E294, 1979). Guinea pig stomach fundus was obtained from male Hartley guinea pigs, 300–350 g, and the mucosa was scraped off with a glass slide. The mucosa was homogenized in 50 mM Tris buffer, pH 7.4, containing 1 mM phenylmethanesulfonyl fluoride using a Dounce glass homogenizer, and the suspension was centrifuged at 40,000 g for 10 min. The resulting pellet was resuspended and centrifuged once more, the final pellet was then suspended in 100 ml assay buffer per 1 guinea pig stomach to give a protein concentration of 200–300 μg/200 μl. The assay buffer consisted of 50 mM Tris buffer, pH 7.4, 5 mM $MgCl_2$, 0.14 mg/ml bacitracin, and 1 μg/ml each of leupeptin, chymostatin, aprotinin and pepstatin. Reagent volumes for the assay were the same as those used for CCK binding to brain membranes. The radioactive ligand was 20 pM $^{125}$I-gastrin I, from DuPont NEN (NEX-176). The samples were incubated 3 hours at room temperature and filtered and counted as described for CCK binding to brain membranes. Compound samples were prepared and IC-50 values were determined as described for the CCK-brain receptor binding. Non-specific binding was determined using 100 nM gastrin I (human synthetic from Sigma Chemical Co.).

Table III below summarizes representative CCK and gastrin-binding tests results for exemplified compounds in accordance with this invention.

TABLE III

CCK and Gastrin Receptor Binding Data

| Compound of Example No. | $IC_{50}$, μM, or Percent Inhibition (at 1 or 10 μM) | | |
|---|---|---|---|
| | Brain | Pancreas | Gastrin |
| 1 | 0.022 | 0.19 | 0.15 |
| 2 | 0.29 | 14(10) | |
| 3 | 0.054 | 34(10) | 1.1 |
| 4 | 0.39 | 78(10) | |
| 5 | 77(10) | 18(10) | |
| 6 | 4.4 | 15(10) | |
| 7 | 1.1 | 81(10) | |
| 8 | 34(10) | 2(10) | |
| 9 | 3.7 | 33(10) | |
| 10 | 57(10) | 4(10) | |
| 11 | 67(10) | | |
| 12 | 0.34 (O—) | 64(10) | |
| | 1.9 (N—) | 55(10) | |
| 13 | 67(10) | | |
| 14 | 2.6 | 60(10) | |
| 15 | 69(10) | 10(10) | |
| 16 | 0.044 | 62(10) | 0.42 |
| 17 | 0.52 | 6(10) | |
| 18 | 0.093 | 22(10) | |
| 19 | 68(10) | 36(10) | |
| 20 | 0.031 | 11.6 | 0.49 |
| 21 | 0.057 | 77(10) | |
| 22 | 42(1) | 27(10) | |
| 23 | 0.49 | 23(10) | |
| 24 | 0.15 | 45(10) | |
| 25 | 0.21 | 14(10) | |
| 26 | 0.075 | 47(10) | |
| 27 | 0.23 | 60(10) | |
| 28 | 0.44 | 55(10) | |
| 29 | 0.025 | 47(10) | 0.26 |
| 30 | 0.031 | 49(10) | 0.35 |
| 31 | 54(1) | 71(10) | |
| 32 | 42(1) | 69(10) | |
| 33 | 0.34 | 20(10) | |
| 34 | 1.5 | 12(10) | |
| 35 | 0.39 | 48(10) | |
| 36 | 0.45 | 33(10) | |
| 37 | 82(1) | 75(10) | |
| 38 | 0.056 | 53(10) | 0.24 |
| 39 | 0.33 | 52(10) | |
| 40 | 0.75 | 38(10) | |
| 41 | 57(10) | 21(10) | |
| 42 | 0.78 | 37(10) | |
| 43 | 0.23 | 24(10) | |
| 44 | 0.26 | 67(10) | |
| 45 | 0.022 | 0.16 | |
| 46 | 0.042 | 1.2 | 0.21 |
| 47 | 0.39 | 51(10) | |
| 48 | 0.080 | 98(10) | |
| 49 | 0.043 | 40(10) | 0.25 |
| 50 | 0.013 | 87(10) | 0.081 |
| 51 | 18(1) | 25(10) | |
| 52 | 60(1) | 21(10) | |
| 53 | 1.2 | 17(10) | |
| 54 | 1.15 | 53(10) | |
| 55 | 0.60 | 47(10) | |
| 56 | 25(1) | 15(10) | |
| 57 | 1.0 | 45(10) | |
| 58 | 10(1) | 85(10) | |
| 59 | 44(1) | 75(10) | |
| 60 | 34(10) | 37(10) | |
| 61 | 56(10) | 78(10) | |
| 62 | 2.2 | 37(10) | |
| 63 | 0.51 | 0.075 | |
| 64 | 5.3 | 34(1) | |
| 65 | 50(10) | 37(10) | |
| 66 | 40(10) | 23(10) | |
| 67 | 46(10) | | |
| 68 | 4.3 | 70(10) | |
| 69 | 0.5 | 12(10) | |
| 70 | 13(1) | 36(10) | |
| 71 | 1.2 | 39(10) | |
| 72 | 88(10) | 22(10) | |
| 73 | 16(10) | 20(10) | |
| 74 | 23(10) | 15(10) | |
| 75 | 60(10) | 40(10) | |
| 76 | 55(10) | 4(10) | |
| 77 | 56(10) | 20(10) | |
| 78 | 1.8 | 49(10) | |
| 79 | 43(10) | 9(10) | |
| 80 | 5.2 | 9(10) | |
| 81 | 95(10) | 59(10) | |
| 82 | 23(10) | | |
| 83 | 37(1) | 12(10) | |
| 84 | 70(10) | 26(10) | |
| 85 | 78(10) | 19(10) | |
| 86 | 1.1 | 58(10) | |
| 87 | 47(10) | 23(10) | |
| 88 | 40(10) | 37(10) | |
| 89 | 34(10) | 21(10) | |
| 90 | 45(1) | 63(10) | |
| 91 | 0.010 | 94(10) | 0.062 |
| 92 | 0.064 | 88(10) | 0.16 |
| 93 | 0.29 | 75(10) | 0.66 |
| 94 | 50(10) | | |
| 95 | 55(10) | 18(10) | |
| 96 | 42(10) | 13(10) | |
| 97 | 42(10) | | |
| 98 | 74(10) | 33(10) | |
| 99 | 3.3 | 86(10) | |
| 100 | 2.2 | 78(10) | |
| 101 | 1.3 | 7(10) | |
| 102 | 4.7 | 11(10) | |
| 103 | 0.87 | 78(10) | |
| 104 | 0.9 | 47(10) | |
| 105 | 0.49 | 43(10) | |
| 106 | 0.19 | 78(10) | 0.87 |
| 107 | 86(10) | 61(10) | |
| 108 | 1.3 | 87(10) | |
| 109 | 6.0 | 11(10) | |
| 110 | 0.007 | 47(10) | 0.13 |
| 111 | 0.020 | 35(10) | 0.61 |
| 112 | 0.072 | 42(10) | 1.4 |
| 113 | 25(1) | 21(10) | |
| 114 | 0.020 | 38(10) | 0.36 |
| 115 | 0.15 | 53(10) | 0.32 |
| 116 | 0.031 | 80(10) | 0.23 |
| 117 | 0.40 | 64(10) | 1.0 |
| 118 | 0.36 | 41(10) | 5.2 |
| 119 | 1.2 | 64(10) | |
| 120 | 0.016 | 87(10) | 0.12 |
| 121 | 0.014 | 26(10) | 0.12 |
| 122 | 0.015 | 8.6 | 0.22 |
| 123 | 0.068 | 23(10) | 0.69 |
| 124 | 0.15 | 36(10) | 0.73 |

TABLE III-continued

CCK and Gastrin Receptor Binding Data

| Compound of Example No. | IC$_{50}$, µM, or Percent Inhibition (at 1 or 10 µM) | | |
|---|---|---|---|
| | Brain | Pancreas | Gastrin |
| 125 | 0.10 | 42(10) | 0.59 |
| 126 | 0.011 | 59(10) | 0.21 |
| 127 | 0.032 | 73(10) | 0.21 |
| 128 | 0.49 | 39(10) | |
| 129 | 0.16 | 69(10) | 0.86 |
| 130 | 0.012 | 42(10) | 0.10 |
| 131 | 0.012 | 61(10) | 0.062 |
| 132 | 0.008 | 48(10) | 0.070 |
| 133 | 0.006 | 7.9 | 0.025 |
| 133A | 0.36 | 55(10) | 1.5 |
| 134 | 0.033 | 75(10) | 0.093 |
| 135 | 0.14 | 18(10) | 1.7 |
| 136 | | | 0.16 |
| 137 | | 0.032 | |
| 138 | | 0.069 | |
| 140 | 0.37 | | |
| 141 | 0.016 | | |
| 142 | | | 0.017 |
| 143 | | | 0.81 |

Antipsychotic Studies

Certain compounds of this invention have been tested in the conditioned avoidance assay in rats. The inhibition of conditioned avoidance behavior has been used as one predictor of antipsychotic activity. R. E. Chipkin, et al., *J. Pharmacol. Exp. Ther.*, 247, 1093–1102 (1988). These studies demonstrated that certain compounds of this invention do not affect conditioned avoidance behavior in rats when tested up to six hours after administration.

However, the same compounds which were tested in the conditioned avoidance assay were tested for their ability to selectively decrease the number of spontaneously active A10 dopamine cells. Atypical antipsychotic compounds are known to selectively decrease the number of spontaneously active A10 dopamine cells. L. A. Chiodo, et al., *J. Neurosci.*, 3, 1607–1619 (1983) and F. J. White et al., *Science*, 221, 1054–1057 (1983). The effect typically requires chronic administration of the antipychotic. Likewise, these atypical antipsychotics normally have a delayed onset of action in clinical use.

Acute administration of the CCK-B antagonists of this invention significantly decreased the number of spontaneously active A10 dopamine neurons. Therefore, these studies support that the CCK-B antagonists of this invention should have therapeutic effects in schizophrenic patients without significant extra-pyramidal side effects, and without a delayed onset of action. (See, Catalepsy Studies for additional discussion).

Catalepsy Studies

Acute administration of classical antipsychotic drugs results in catalepsy. Production of catalepsy is thought to be predictive of Parkinson-like extrapyramidal side effects. Sanberg, et al., *Neuroscience* 102:748–759 (1988). Applicants have discovered that compounds of this invention do not produce catalepsy, as illustrated in Table IV. Haloperidol, a classical anti-psychotic, was used as a reference.

TABLE IV

| Compound | Dose (mg/kg) | Catalepsy Score (secs) | | | |
|---|---|---|---|---|---|
| | | Pre | 60 Min | 120 Min | 180 Min |
| Vehicle | | 0.9 ± 0.2 | 1.6 ± 0.4 | 1.8 ± 0.5 | 3.7 ± 0.8 |
| Example 141 | 10 | 1.1 ± 0.2 | 3.8 ± 0.9 | 3.3 ± 1.2 | 4.6 ± 2.1 |
| | 30 | 1.5 ± 0.3 | 2.6 ± 1.1 | 2.0 ± 0.6 | 4.9 ± 1.9 |
| Haloperidol | 0.25 | 1.8 ± 1.1 | 2.2 ± 0.3 | 9.9 ± 2.7* | 23.1 ± 4.9* |
| | 0.5 | 0.9 ± 0.2 | 3.3 ± 1.7 | 17.6 ± 2.2* | 33.5 ± 8.3* |
| | 1.0 | 1.2 ± 0.4 | 10.6 ± 6.3* | 100.0 ± 46.2* | 123.9 ± 39.7* |

*Significantly different from vehicle control, $P < 0.001$

Further, compounds of this invention were evaluated for their ability to block haloperidol-induced catalepsy. As illustrated in Table V, all of the tested compounds blocked haloperidol-induced catalepsy within two hours after haloperidol treatment. Thus, these compounds may be useful for the treatment of neuroleptic disorders including dystonia, dyskinesia, akathisia, and Parkinsonism. Preferred compounds for treatment of neuroleptic related disorders are compounds of formula (I). More preferredly, R and R$^1$ are trans. Most preferred compounds are compounds of formula (I) wherein R and R$^1$ are phenyl or substituted phenyl.

TABLE V

| Pretreatment 30 mg/kg | Test Cmpd. 0.5 gm/kg | Catalepsy Score (secs) | | | |
|---|---|---|---|---|---|
| | | Pre | 60 Min | 120 Min | 180 Min |
| Vehicle | Hal | 3.12 ± 0.61 | 9.72 ± 2.1 | 27.42 ± 6 | 30.61 ± 6.4 |
| Compound 1 | Hal | 2.35 ± 0.5 | 7.35 ± 0.6 | 12.46 ± 2.9* | 10.96 ± 1.7* |
| Compound 2 | Hal | 1.88 ± 0.5 | 4.53 ± 1.1* | 7.3 ± 1.8* | 7.1 ± 2.1* |
| Compound 3 | Hal | 2.4 ± 0.6 | 5.6 ± 1.5 | 11.6 ± 2* | 11.0 ± 3.4* |
| Compound 4 | Hal | 1.6 ± 0.4 | 6.8 ± 1.6 | 15.8 ± 3.3* | 15.8 ± 4.3* |

*Significantly different from vehicle control, $P < 0.05$

Test Procedures for Catalepsy Studies

Male Sprague-Dawley rats (290–350 g) were used in these studies. Catalepsy was evaluated using the bar test (Sanberg et al., *Neurosci.*, 102,748–759, (1988); Ferre, et al., *Pharm. Biochem. Beh.*, 35, 753–757 (1990). The bar apparatus consisted of a horizontal metal rod with a diameter of 1 cm, which was positioned 10 cm from the floor to the top of the bar. The animal was gently placed in front of the bar, and then its forepaws were lifted to rest on the bar. The length of time, in seconds, until both forepaws touched the floor (3 minutes maximum allowed) was recorded. A baseline measurement was taken prior to injection, and catalepsy was evaluated every 60 minutes for three hours after injection of the compounds (Table IV). In a separate set of experiments, the compounds of this invention were administered 60 minutes prior to the administration of haloperidol, and catalepsy was evaluated every 60 minutes for three hours after the haloperidol injection. Catalepsy scores of drug-treated animals were compared to haloperidol- or vehicle-treated animals at each time point using the analysis of variance (ANOVA) (Table V). Haloperidol (Research Biochemicals Inc.) was dissolved in distilled water and a small amount of 0.1N lactic acid. The compounds of this invention were prepared in 50% ethanol. The volume of all injections was 1 ml/kg.

Benzodiazepine and Nicotine Withdrawal

In humans, withdrawal from the chronic administration of benzodiazepines or nicotine can result in a variety of undesirable side-effects, including anxiety. In animals, benzodiazepine withdrawal has also been demonstrated to have anxiogenic effects as indicated by decreases in body weight and food intake (Goudie and Leathley, *European Journal of Pharmacology*, 185, 179–187, 1990), disruption of an operant behavior (Goudie and Leathley, *Psychopharmacology*, 109, 461–465, 1992), decreased time spent in the light compartment of a light/dark box (Costall et al., *Pharmacology, Biochemistry and Behavior*, 36, 97–104, 1990), decreased time spent in the open arms of an elevated plus-maze (Andrews and File, *Psychopharmacology*, 108, 333–337, 1992), and increased auditory startle responses (Martinez et al., *Pharmacology, Biochemistry and Behavior*, 41, 461–464, 1992). Withdrawal from chronic nicotine administration also has anxiogenic effects as indicated by decreased time spent in the light compartment of a light/dark box (Costall et al., Ibid) and increased auditory startle responses. Applicants examined the effects of compounds of this invention on the auditory startle response of rats undergoing withdrawal from the chronic administration of diazepam or nicotine. As has been observed previously, cessation of chronic diazepam or nicotine administration resulted in significantly increased auditory startle responses. Administration of compounds of this invention, 60 minutes prior to startle testing at doses that do not affect baseline startle responding, significantly attenuated the diazepam- and nicotine-withdrawal-induced increases in startle responding.

These results indicate that compounds of this invention will be effective in the treatment for benzodiazepine and nicotine withdrawal symptoms in vertebrates. The compounds are most preferredly used for the treatment of humans. The preferred compounds for treating nicotine withdrawl or benzodiazepine withdrawal are compounds of formula (I). More preferredly, the R and $R^1$ substituents are trans. The most preferred compounds for said treatment are compounds wherein R and $R^1$ are each phenyl or substituted phenyl.

Procedures for Benzodiazepine and Nicotine Withdrawal Studies

Animals

Male Long Evans rats (200–220 g; Harlan Sprague Dawley, Columbus, Ind.) were individually housed in a controlled environment on a 12 hour light-dark cycle and were given free access to food (Purina Rodent Chow) and water. All treatment groups contained 8–10 rats.

Chronic Drug Treatment

Rats were anesthetized with halothane and Alzet osmotic minipumps (Alza Corporation, Palo Alto, Calif., Model 2ML2) were implanted subcutaneously. Diazepam (Sigma Chemical; St. Louis, Mo.) was suspended in 40% polyethylene glycol, 10% ethanol and Tween 80. Nicotine ditartrate was dissolved in physiological saline. Pumps were filled with either diazepam (20 mg/kg/day), nicotine ditartrate (6 mg/kg base/day), or the appropriate vehicle. Twelve days following implantation of pumps, rats were anesthetized with halothane and the pumps were removed.

Auditory Startle Response

The sensory motor reactions [auditory startle response (peak amplitude, Vmax)] of individual rats was recorded using San Diego Instruments startle chambers (San Diego, Calif.). Startle sessions consisted of a 5-minute adaptation period at a background noise level of 70±2 dBA immediately followed by 25 presentations of auditory stimuli (120±3 dBA noise, 50 ms duration) presented at 8-second intervals. Peak startle amplitudes were then averaged for all 25 presentations of stimuli for each session. Auditory startle responding was evaluated daily at 24 hour intervals on days 1–4 following drug withdrawal.

Results

The compound of Example 141 was administered 60 minutes before startle testing at doses of 0, 10, 30, 60, or 100 mg/kg. Administration of 60 mg/kg and 100 mg/kg of the compound significantly reduced the benzodiazepine withdrawal-induced increase in sensory responsiveness on all days examined.

The administration of 10 mg/kg of the Example 141 compound significantly reduced the nicotine withdrawal-induced increase in startle response on all days except day 4. The administration of the compound at doses of 30 mg/kg and 60 mg/kg significantly reduced the nicotine withdrawal-induced increase in sensory responsiveness on all days examined.

Gastrointestinal Studies

Compounds of this invention are useful for the treatment of neoplasms of gastrointestinal origin. The preferred compounds for the treatment of gastrointestinal tumors are compounds of formula (I). More preferredly, the R and $R^1$ substituents are trans. The most preferred compounds for said treatment are compounds wherein R and $R_1$ are each phenyl or substituted phenyl. Most preferredly the patient is a human. Examples of neoplasms of gastrointestinal origin include malignant or benign tumors of the stomach, pancreas, intestines, or colon.

Certain compounds of this invention have CCK antagonist activity which inhibits CCK-induced gastrointestinal motility without any significant reduction in CCK-induced gall bladder emptying. Such compounds are particularly useful for the treatment or prevention of gastrointestinal conditions including irritable bowel syndrome, non-ulcer dyspepsia, and idiopathic constipation, without the undesired side-effect of gall bladder statis.

The most preferred compound of the invention having CCK antagonist activity without affecting CCK-induced gall bladder emptying is (±)-trans-1-phenylaminocarbonyl-4,5-diphenyl-3-pyrazolidinone (Example 15).

Procedures to Study Gall Bladder Emptying and Colonic Motility

Experiments were performed on fasted (18 hour) male ferrets weighing 0.8–1.5 kilograms (Triple F Supplier) and water was given ad lib. Anesthesia was induced with urethane (0.2 ml/100 grams body weight j.p., Sigma Chemical Company), a tracheal tube was inserted to provide a clear airway for spontaneous breathing and the body temperature was maintained at 38° using a homeothermic blanket (Harvard Apparatus). The left jugular vein was cannulated (PE-50, i.d. 0.58 mm, o.d. 0.97 mm) for the subsequent administration of drugs and the left carotid artery was cannulated (PE-90, i.d. 0.86 mm, o.d. 1.277 mm) for the continual measurement of blood pressure and heart rate. Following a laporatomy, a catheter (PE-50) was inserted into the gall bladder through the bile duct and connected via a pressure transducer to a chart recorder for the visual display. The colon was located and a strain gauge transducer was sutured in the circular muscle direction to monitor contractile state. Before each experiment the blood pressure, heart rate and all motility recording transducers were calibrated for subsequent recording of data.

Experimental Protocol

Following a 30 minute stabilization period, cholecystokinin 8-sulfated (CCK8-S) was given at doses of 100, 300 and 700 ng/kg intravenously (iv), with a 10 minute stabilization period in between CCK8-S doses. The test compound was administered (iv) after another 30 minute stabilization period, and the CCK8-S dose-response curve was repeated five minutes later.

Test compound vehicle was 3 drops of DMSO (99.9%), 0.5 ml 0.1N NaOH, saline.

At the 1 mg/kg dose, (±)-trans-1-phenylaminocarbonyl-4,5-diphenyl-3-pyrazolidinone inhibited CCK-induced (300 ng/kg)colonic motility by 57%. In contrast, the gall bladder emptying was not measurably altered. Further, when CCK-8 was administered at 100 ng/kg, colonic motility was inhibited by nearly 75% while CCK-induced gall bladder emptying was altered by about 10%%. Thus, compounds of this invention produce the desired effect of inhibiting CCK-induced colonic motility without significantly altering CCK-induced gall bladder emptying. The term "significantly" means less than about 12% variation from the control.

Preferred compounds inhibit CCK-induced colonic motility by about 15% or more. Likewise, preferred compounds alter gall bladder emptying by about 10% or less. The more desired compounds for the treatment of idiopathic constipation, colonic hypermotility, non-ulcer dyspepsia, and irritable bowel syndrome will inhibit gall bladder emptying by about 10% or less than the level of the control and inhibit colonic motility by about 20% or more than the control. The most preferred compounds for said treatment will inhibit gall bladder emptying by about 10% or less and inhibit colonic motility by about 25% or more. Especially preferred compounds inhibit gall bladder emptying by about 10% or less and inhibit colonic motility by about 34% to about 70%.

We claim:

1. A method for treating or preventing a condition associated with cholecystokinin modulation in a warm blooded vertebrate, comprising administering an effective amount of a compound of the formula

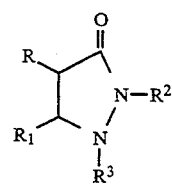

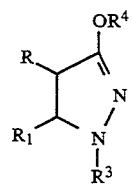

wherein

R and $R^1$ are independently hydrogen, $C_1$-$C_6$ alkyl, phenyl, benzyl, naphthyl, pyridyl or substituted phenyl having 1, 2, or 3 substituents selected from the group consisting of $C_1$-$C_6$ alkyl, $C_1$-$C_6$ alkoxy, $C_1$-$C_6$ alkylthio, halo, trifluoromethyl, phenyl, phenoxy, phenyl($C_1$-$C_4$ alkyl), phenyl($C_1$-$C_4$ alkoxy), phenylacetyl, $C_1$-$C_6$ alkanoyl, cyano, carbamyl, nitro, $C_1$-$C_6$ alkoxycarbonyl, methylenedioxy, $C_3$-$C_6$ alkylene, amino, —NH($C_1$-$C_4$ alkyl or benzyl), and N($C_1$-$C_4$ alkyl)$_2$;

$R^2$ is hydrogen, $C_1$-$C_6$ alkyl, carboxymethyl, $C_1$-$C_4$ alkoxycarbonylmethyl or a group of the formula

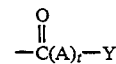

wherein t is 1 or 0;

A is —$CH_2$—, —O—, —NH— or —N($C_1$-$C_6$ alkyl)—; and

Y is phenyl or substituted phenyl as defined above;

$R^4$ is $C_1$-$C_6$ alkyl, carboxymethyl, or $C_1$-$C_4$ alkoxycarbonylmethyl;

$R^3$ is hydrogen or a group of the formula

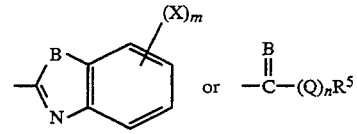

wherein

B is 0 or S;

X is selected from the phenyl substituents defined above;

m is 0, 1 or 2;

n is 0 or 1;

Q is —NH—, —N($C_1$-$C_6$ alkyl)—, —S—, or —O—; and $R^5$ is a group of the formula —[CH($R^6$)]$_q$—(CH$_2$)$_r$—$R^7$ wherein $R^6$ is hydrogen or $C_1$-$C_6$ alkyl;

q is 0 or 1;

r is 0, 1 or 2; and $R^7$ is hydrogen, $C_1$-$C_8$ alkyl, $C_3$-$C_8$ cycloalkyl, pentafluorophenyl, pyridyl, tetrahydro-naphthyl, indolyl, quinolinyl, phenyl, naphthyl, or phenyl or naphthyl substituted with 1, 2 or 3 substituents as defined above for phenyl; or the group —(Q)$_n$R$^5$ is 2-tetrahydroisoquinolinyl; and the pharmaceutically acceptable salts thereof; provided that at least one of the group R or R$^1$ is other than hydrogen or C$_1$-C$_6$ alkyl, and R or R$^1$ is hydrogen only when the other of R and R$^1$ is substituted phenyl in which the substituent is phenyl; and provided further that at least one of the groups R$^2$ and R$^3$ is other than hydrogen, and when R$^3$ is a group of the formula

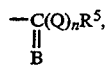

R$^2$ is other than a group of the formula

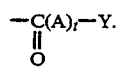

2. A method of claim 1 wherein the condition is a response produced by cessation and withdrawal from the use of a benzodiazepine.

3. A method of claim 1 wherein the condition is a response produced by cessation and withdrawal from the use of nicotine.

4. A method of claim 1 wherein the condition is a neuroleptic related disorder.

5. A method of claim 4 wherein the neuroleptic related disorder is selected from the group consisting of dystonia, dyskinesia, akathisia, and Parkinsonism.

6. A method of claim 1 wherein the condition is a psychosis.

7. A method of claim 6 wherein the condition is selected from the group consisting of Moderate Mental Retardation; Severe Mental Retardation; Profound Mental Retardation; Autistic Disorder; Pervasive Development Disorder NOS; Conduct Disorder, Group Type; Conduct Disorder, Solitary Agressive Type; Tourette's Disorder; Primary Degenerative Dementia of the Alzheimer Type, Senile Onset, with Delirium; Primary Degenerative Dementia of the Alzheimer Type, Senile Onset, with Delusions; Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis);Bipolar Disorder, Hixed, with Psychotic Features; Bipolar Disorder, Hanic, with Psychotic Features; Bipolar Disorder, Depressed, with Psychotic Features; Bipolar Disorder NOS; Personality Disorders, Paranoid; Personality Disorders, Schizotypal; and Personality Disorders, Borderline.

8. A method of claim 7 wherein the condition is selected from the group consisting of Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis);Bipolar Disorder, Mixed, with Psychotic Features; Bipolar Disorder, Manic, with Psychotic Features; Bipolar Disorder, Depressed, with Psychotic Features; Bipolar Disorder NOS; with Psychotic Features; Personality Disorders, Paranoid; Personality Disorders, Schizotypal; and Personality Disorders, Borderline.

9. A method of claim 8 wherein the condition is selected from the group consisting of Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; and Personality Disorders, Schizotypal.

10. A method of claim 1 wherein the condition is an anxiety disorder.

11. A method of claim 10 wherein the condition is selected from the group consisting of Anxiety Disorders, Panic Disorder, Panic Disorder with Agoraphobia, Panic Disorder without Agoraphobia , Agoraphobia without History of Panic Disorders, Social Phobia, Simple Phobia, Obsessive Compulsive Disorder , Post-Traumatic Stress Disorder, Generalized Anxiety Disorder, Anxiety Disorder NOS, Organic Anxiety Disorder , Psychoactive Substance Anxiety Disorder, Separation Anxiety Disorder, Avoidant Disorder of Childhood or Adolescence , and Overanxious Disorder.

12. A method of claim 11 wherein the condition is selected from the group consisting of Panic Disorder; Social Phobia; Simple Phobia; Organic Anxiety Disorder; Obsessive Compulsive Disorder; Post-traumatic Stress Disorder; Generalized Anxiety Disorder; and Anxiety Disorder NOS.

13. A method of claim 1 wherein the condition is a pathological psychological condition wherein delusions, hallucinations, disorganized behavior, or anxiety are a consistent manifestation of the pathological condition.

14. A method for treating or preventing a functional bowel disorder associated with motility disorders in a warm-blooded vertebrate comprising administering an effective amount of a compound of the formula

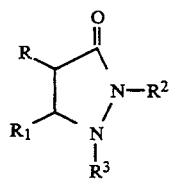

I or

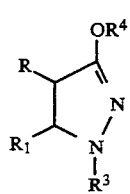

II wherein

R and $R^1$ are independently hydrogen, $C_1$–$C_6$ alkyl, phenyl, benzyl, naphthyl, pyridyl or substituted phenyl having 1, 2, or 3 substituents selected from the group consisting of $C_1$–$C_6$ alkyl, $C_1$–$C_6$ alkoxy, $C_1$–$C_6$ alkylthio, halo, trifluoromethyl, phenyl, phenoxy, phenyl($C_1$–$C_4$ alkyl), phenyl($C_1$–$C_4$ alkoxy), phenylacetyl, $C_1$–$C_6$ alkanoyl, cyano, carbamyl, nitro, $C_1$–$C_6$ alkoxycarbonyl, methylenedioxy, $C_3$–$C_6$ alkylene, amino, —NH($C_1$–$C_4$ alkyl or benzyl), and N($C_1$–$C_4$ alkyl)$_2$;

$R^2$ is hydrogen, $C_1$–$C_6$ alkyl, carboxymethyl, $C_1$–$C_4$ alkoxycarbonylmethyl or a group of the formula

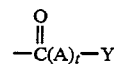

wherein t is 1 or 0;

A is —CH$_2$—, —O—, —NH— or —N($C_1$–$C_6$ alkyl)—; and

Y is phenyl or substituted phenyl as defined above;

$R^4$ is $C_1$–$C_6$ alkyl, carboxymethyl, or $C_1$–$C_4$ alkoxycarbonylmethyl;

$R^3$ is hydrogen or a group of the formula

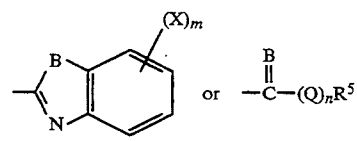

wherein

B is O or S;

X is selected from the phenyl substituents defined above; m is 0, 1 or 2;

n is 0 or 1;

Q is —NH—, —N($C_1$–$C_6$ alkyl )—, —S—, or —O—; and $R^5$ is a group of the formula —[CH($R^6$)]$_q$—(CH$_2$)$_r$—$R^7$ wherein $R^6$ is hydrogen or $C_1$–$C_6$ alkyl;

q is 0 or 1;

r is 0, 1 or 2; and $R^7$ is hydrogen, $C_1$–$C_8$ alkyl, $C_3$–$C_8$ cycloalkyl, pentafluorophenyl, pyridyl, tetrahydro-naphthyl, indolyl, quinolinyl, phenyl, naphthyl, or phenyl or naphthyl substituted with 1, 2 or 3 substituents as defined above for phenyl; or the group —(Q)$_n$R$^5$ is 2-tetrahydroisoquinolinyl; and the pharmaceutically acceptable salts thereof;

provided that at least one of the group R or $R^1$ is other than hydrogen or $C_1$–$C_6$ alkyl, and R or $R^1$ is hydrogen only when the other of R and $R^1$ is substituted phenyl in which the substituent is phenyl; and provided further that at least one of the groups $R^2$ and $R^3$ is other than hydrogen, and when $R^3$ is a group of the formula

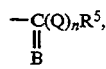

$R^2$ is other than a group of the formula

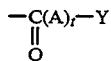

provided that the gastrointestinal disorder is not irritable bowel syndrome.

15. A method of claim 14 wherein the disorder is selected from the group consisting of colonic hypermotility, non-ulcer dyspepsia, and idiopathic constipation.

16. A method of claim 15 wherein the disorder is non-ulcer dyspepsia or idiopathic constipation.

17. A method of claim 15 wherein the compound inhibits CCK-induced colonic motility and does not significantly alter CCK-induced gall bladder emptying.

18. A method of claim 14 wherein the compound is (±)-trans-1-phenylaminocarbonyl-4,5-diphenyl-3pyrazolidinone.

19. A method of claim 18 wherein the disorder is non-ulcer dyspepsia or idiopathic constipation.

* * * * *

UNITED STATES PATENT AND TRADEMARK OFFICE
CERTIFICATE OF CORRECTION

PATENT NO. : 5,399,565

DATED : March 21, 1995

INVENTOR(S) : Beverly Greenwood et al.

It is certified that an error appears in the above-identified patent and that said Letters Patent is hereby corrected as shown below:

Column 3, line 47, "r is 0, 1, or and $R^7$ is hydrogen, $C_1$-$C_8$ alkyl, $C_3$-8" should read, -- r is 0, 1, or 2; and $R^7$ is hydrogen, $C_1$-$C_8$ alkyl, $C_3$-$C_8$ --.

Column 4, structure, "$-C(A)_t-Y$" should read, -- $-C(A)_t-Y$ --.
                         $\|$                                $\|$
                         B                                    O Column 6, line 35, "Hood Disorder" should read, -- Mood Disorder --.

Column 10, lines 57-58, "$R^1$-H=C(-R)-COOR'" should read, -- $R^1$-H=C(R)-COOR' --.

Column 14, line 53, "$C_{22}H_{17}C_1N_2O_3$" should read, -- $C_{22}H_{17}ClN_2O_3$ --.

Column 15, line 48, "$C_{22}H_{16}C_1N_3OS$" should read, -- $C_{22}H_{16}ClN_3OS$ --.

Column 19, example 15 under Formula, delete 73.84.

Column 19, example 15 under Analysis % Found, C/H/N, "5.42, 11.75" should read, -- 73.84, 5.42, 11.75 --.

Column 20, example 23 under Formula, insert -- $C_{24}H_{21}N_3O_3$ --.

Column 21, example 28 under 1HNMR, "7.30(d,J=12Hz, 2H)" should read, -- 7.03 --.

Column 22, example 35 under R, "4-O-t-Br" should read, -- 4-O-i-Pr --.

Column 23, example 39 under Analysis % Found, C, "65,07" should read, -- 65.07 --.

Column 23, example 40 under Formula, "$C_{22}H_{19}N_4O_4$" should read, -- $C_{22}H_{18}N_4O_4$ --.

Column 23, example 40 under Analysis % Found, C/H/N, insert 65.53, 4.25, 13.67.

Column 25, example 55 under Analysis % Found, C, "62.15" should read, -- 62.16 --.

UNITED STATES PATENT AND TRADEMARK OFFICE
CERTIFICATE OF CORRECTION

PATENT NO. : 5,399,565

DATED : March 21, 1995

INVENTOR(S) : Beverly Greenwood et al.

It is certified that an error appears in the above-identified patent and that said Letters Patent is hereby corrected as shown below:

Column 26, example 57 under 1HNMR, "72-7.5(m, 14H)" should read, -- 7.2-7.5(m, 14H) --.

Column 26, example 59 under 1HNMR, "7.15-7.55(m, 10H)" should read, -- 7.15-7.5(m, 10H) --.

Column 27, example 61 under Analysis % Found, C, "6.87" should read, -- 62.87 --.

Column 29, example 68 under Analysis % Found, C, "52.20" should read, -- 62.20 --.

Column 31, example 71 under 1HNMR, "0.9(t, J=9HZ, 3H)" should read, -- 0.95(t, J=9HZ, 3H) --.

Column 33, example 76 under Analysis % Found, C, "57.76" should read, -- 67.76 --.

Column 33, example 78 under Formula, "C23H19Cl2N2O2" should read, --C23H18Cl2N2O2--

Column 33, example 79 under Formula, "C22H19N2O3" should read, -- C22H18N2O3 --.

Column 33, example 81 under Analysis % Found, N, "6.06" should read, -- 6.07 --.

Column 36, example 86 under Formula, "C22H14Cl2N3O5" should read, --C22H14Cl2N3O5--

Column 37, example 89 under 1HNMR, "7.18-7.3(m, 10H)" should read, -- 7.18-7.35(m, 10H) --.

Column 37, example 91 under Formula, "C26H12N3O2" should read, -- C26H21N3O2 --.

Column 39, example 102 under 1HNMR, "10.56(s, 1H)" should read, --10.58(s, 1H) --.

Column 40, example 106 under 1HNMR, "5.95-7.4" should read, -- 6.95-7.4 --.

Column 42, example 113 under Analysis % Found C, "64.25" should read, -- 64.26 --.

UNITED STATES PATENT AND TRADEMARK OFFICE
CERTIFICATE OF CORRECTION

PATENT NO. : 5,399,565

DATED : March 21, 1995

INVENTOR(S) : Beverly Greenwood et al.

It is certified that an error appears in the above-identified patent and that said Letters Patent is hereby corrected as shown below:

Column 49, line 55, "retrogan" should read, -- nitrogen --.

Column 50, line 6, "pate yellow" should read, -- pale yellow --.

Column 52, line 28, "then time solvents" should read, -- then the solvents --.

Column 54, line 4, "glycol his(2-amino" should read, -- glycol bis(2-amino --.

Column 64, line 9, "order, Hixed, with" should read, -- order, Mixed, with --.

Column 64, line 10, "Hanic, with" should read, -- Manic, with --.

Signed and Sealed this

Second Day of April, 1996

Attest:

BRUCE LEHMAN

Attesting Officer

Commissioner of Patents and Trademarks